United States Patent
Story et al.

(10) Patent No.: US 12,420,113 B2
(45) Date of Patent: Sep. 23, 2025

(54) METHODS AND APPARATUS FOR APPLYING TUMOR TREATING FIELDS COMBINED WITH PERSONALIZED ULTRA-FRACTIONATED STEREOTACTIC ADAPTIVE RADIOTHERAPY

(71) Applicant: THE BOARD OF REGENTS OF THE UNIVERSITY OF TEXAS SYSTEM, Austin, TX (US)

(72) Inventors: Michael D. Story, Dallas, TX (US); Debabrata Saha, Carrollton, TX (US); Narasimha Kumar Karanam, Dallas, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 238 days.

(21) Appl. No.: 18/194,513

(22) Filed: Mar. 31, 2023

(65) Prior Publication Data

US 2023/0347173 A1  Nov. 2, 2023

Related U.S. Application Data

(60) Provisional application No. 63/362,369, filed on Apr. 1, 2022.

(51) Int. Cl.
*A61N 5/10* (2006.01)
*A61K 31/4725* (2006.01)
*A61P 35/00* (2006.01)

(52) U.S. Cl.
CPC ........ *A61N 5/1031* (2013.01); *A61K 31/4725* (2013.01); *A61N 5/1039* (2013.01); *A61P 35/00* (2018.01)

(58) Field of Classification Search
CPC ............... A61N 5/1031; A61N 5/1039; A61N 1/36002; A61N 1/40; A61N 5/1038; A61K 31/4725; A61P 35/00
See application file for complete search history.

(56) References Cited

U.S. PATENT DOCUMENTS

| 6,868,289 B2 | 3/2005 | Palti |
| 7,016,725 B2 | 3/2006 | Palti |
| 7,089,054 B2 | 8/2006 | Palti |
| 7,136,699 B2 | 11/2006 | Palti |

(Continued)

FOREIGN PATENT DOCUMENTS

| TW | 201136934 A | 11/2011 |
| WO | 2009117484 A2 | 9/2009 |

(Continued)

OTHER PUBLICATIONS

Mun et al., "Tumor-Treating Fields: A Fourth Modality in Cancer Treatment," Clinical Cancer Research, vol. 24, No. 2, pp. 266-275. (Year: 2018).*

(Continued)

*Primary Examiner* — Kiho Kim
(74) *Attorney, Agent, or Firm* — DLA Piper LLP US

(57) ABSTRACT

A method of treating a tumor in a subject, the method comprises applying a tumor treating field to the tumor at a frequency between approximately 50 kHz and approximately 1,000 kHz; and delivering personalized ultra-fractionated adaptive radiotherapy (PULSAR) regimen.

19 Claims, 21 Drawing Sheets

(56) References Cited

U.S. PATENT DOCUMENTS

| | | |
|---|---|---|
| 7,146,210 B2 | 12/2006 | Palti |
| 7,333,852 B2 | 2/2008 | Palti |
| 7,467,011 B2 | 12/2008 | Palti |
| 7,519,420 B2 | 4/2009 | Palti |
| 7,565,205 B2 | 7/2009 | Palti |
| 7,565,206 B2 | 7/2009 | Palti |
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| RE43,618 E | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,244,345 B1 | 1/2016 | Ishimaru et al. |
| 9,440,068 B2 | 9/2016 | Palti et al. |
| 9,655,669 B2 | 5/2017 | Palti et al. |
| 9,750,934 B2 | 9/2017 | Palti et al. |
| 10,188,851 B2 | 1/2019 | Wenger et al. |
| 2007/0239213 A1 | 10/2007 | Palti |
| 2011/0053977 A1 | 3/2011 | Cress et al. |
| 2012/0035244 A1 | 2/2012 | Chinnaiyan et al. |
| 2016/0129282 A1 | 5/2016 | Yin et al. |
| 2017/0093277 A1 | 3/2017 | Wasserman et al. |
| 2017/0209579 A1 | 7/2017 | Curley et al. |
| 2017/0215939 A1 | 8/2017 | Palti et al. |
| 2017/0281934 A1 | 10/2017 | Giladi et al. |
| 2017/0319256 A1 | 11/2017 | Kang et al. |
| 2018/0001075 A1 | 1/2018 | Kirson et al. |
| 2018/0001078 A1 | 1/2018 | Kirson et al. |
| 2018/0008708 A1 | 1/2018 | Giladi et al. |
| 2018/0050200 A1 | 2/2018 | Wasserman et al. |
| 2018/0160933 A1 | 6/2018 | Urman et al. |
| 2018/0202991 A1 | 7/2018 | Giladi et al. |
| 2019/0022411 A1 | 1/2019 | Parry et al. |
| 2019/0298982 A1 | 10/2019 | Story et al. |
| 2019/0307781 A1 | 10/2019 | Krex et al. |
| 2019/0345566 A1 | 11/2019 | Khera et al. |
| 2020/0297286 A1 | 9/2020 | Costa et al. |
| 2021/0027878 A1 | 1/2021 | He et al. |
| 2021/0292741 A1 | 9/2021 | Story et al. |
| 2023/0347173 A1 | 11/2023 | Story et al. |

FOREIGN PATENT DOCUMENTS

| | | |
|---|---|---|
| WO | 2011101417 A1 | 8/2011 |
| WO | 2012146936 A1 | 11/2012 |
| WO | 2013071415 A1 | 5/2013 |
| WO | 2019025440 A1 | 2/2019 |
| WO | 2019075391 A1 | 4/2019 |
| WO | 2019238873 A1 | 12/2019 |
| WO | 2020160213 A1 | 6/2020 |
| WO | 2021051089 A1 | 3/2021 |

OTHER PUBLICATIONS

Hoyer et al, "The evolution of radiotherapy techniques in the management ofprostate cancer,", Acta Oncologica, vol. 54, pp. 821-824. (Year: 2015).*

Kim EH, Kim YJ, Song HS, Jeong YK, Lee JY, Sung J, Yoo SH, Yoon M. Biological effect of an alternating electric field on cell proliferation and synergistic antimitotic effect in combination with ionizing radiation. Aug. 19, 2016. Oncotarget, vol. 7 No. 38, 62267¬62279. (Year: 2016).

Kirson ED, Schneiderman RS, Dbaly V, Tovarys F, Vymazal J, Itzhaki A, Mordechovich D, Gurvich Z, Shmueli E, Goldsher D, Wasserman Y, Palti Y. Chemotherapeutic treatment efficacy and sensitivity are increased by adjuvant alternating electric fields TRFields). BMC Medical Physics 2009, 9:1. (Year: 2009).

Cavanagh et al., "The role of BRCA1 and BRACA2 mutations in prostate, pancreatic and stomach cancers," Hereditary Cancer in Clinical Practice, vol. 13, No. 16, 2015.

Cescutti et al., "TopBP1 functions with 53BP1 in the G1 DNA damage checkpoint," The EMBO Journal, vol. 29, pp. 3723-3732, 2010.

Chan et al., "Replication stress induces sister-chromatid bridging at fragile site loci in mitosis," Nature Cell Biology, vol. 11, No. 6, pp. 753-775, May 2009.

Das et al., "Non-Small Cell Lung Cancers with Kinase Domain Mutations in the Epidermal Growth Factor Receptor are Sensitive to Ionizing Radiation," Cancer Res., vol. 66, No. 19, pp. 9601-9608, Oct. 2006.

Davies et al., "Tumor treating fields: a new frontier in cancer therapy," Annals of the New York Academy of Sciences, 1291, pp. 86-95, 2013.

Ding et al., "Enhanced identification and biological validation of differential gene expression via Illumina whole-genome expression arrays through the use of the model-based background correction methodology," Nucleic Acids Res., vol. 36, No. 10, p. e58, May 2008.

Foucquier et al., "Analysis of drug combinations: current methodological landscape," Pharmacology Research & Perspectives, vol. 3, Issue 3, p. e00149, 2015.

Geary et al., "Understanding synergy," Am. J. Physiol. Endocrinol. Metab., vol. 304, pp. E237-E253, Dec. 2012.

Gera et al., "Tumor Treating Fields Perturb the Localization of Septins and Cause Aberrant Mitotic Exit," Plos One, DOI:10.371, May 2015.

Giladi et al., "Alternating Electric Fields (Tumor-Treating Fields Therapy) Can Improve Chemotherapy Treatment Efficacy in Non-Small Cell Lung Cancer Both In Vitro and In Vivo," Seminars in Oncology, vol. 41, No. 5, Suppl. 6, pp. S35-S41, Oct. 2014.

Giladi et al., "Mitotic disruption and reduced clonogenicity of pancreatic cancer cells in vitro and in vivo by tumor fields," Pancreatology, vol. 14, pp. 54-63, 2014.

Giladi et al., "Mitotic Spindle Disruption by Alternating Electric Fields Leads to Improper Chromosome Segregation Mitotic Catastrophe in Cancer Cells," Scientific Reports, vol. 5, No. 1, pp. 1-16, Dec. 2015.

Gonzalez et al., "Harnessing dielectric forces for separations of cells, fine particles and macromolecules," Journal of Chromatogrpahy A, vol. 1079, pp. 59-68, Apr. 2005.

Huyen et al., "Methylated lysine 79 of histone H3 targets 53BP1 to DNA double-strand breaks," Nature, vol. 432, pp. Nov. 2004.

Inui et al., "Case Report: A Non-small Cell Lung Cancer Patient Treated with GcMAF, Sonodynamic Therapy and Treating Fields," Anticancer Research, vol. 36, pp. 3767-3770, 2016.

Kaelin, "The Concept of Synthetic Lethality in the Context of Anticancer Therapy," Nature Reviews Cancer, vol. 5, 689-698, Sep. 2005.

Kan et al., "BRCA1 Mutation: A Predictive Marker for Radiation Therapy?," Int. J. Radiat. Oncol. Biol. Phys., vol. 93, No. 2, pp. 281-293, Oct. 2015.

International Search Report of the Inernational Searching Authority issued in International Application No. PCT/US2023/065242, 9 pages, dated Oct. 3, 2023.

(56) References Cited

OTHER PUBLICATIONS

Kirson et al., "Alternating electric fields (TTFields) inhibit metastatic spread of solid tumors to the lungs," Clin. Exp. Metastasis, vol. 26, pp. 633-640, Apr. 2009.
Kirson et al., "Alternating electric fields arrest cell proliferation in animal tumor models and human brain tumors," PNAS, vol. 104, No. 24, pp. 10152-10157, Jun. 2007.
International Search Report and Written Opinion of the Inernational Searching Authority issued in International Application No. PCT/US2020/050745, 8 pages, dated Dec. 7, 2020.
Kirson et al., "Disruption of Cancer Cell Replication by Alternating Electric Fields," Cancer Research, vol. 64, pp. 3288-3295, May 2004.
Lehar et al., "Chemical combination effects predict connectivity in biological systems," Molecular Systems Biology, vol. 3, No. 80, 2007.
McPherson et al., "A role for Brca1 in chromosome end maintenance," Human Molecular Genetics, vol. 15, No. 6, pp. 831-838, Jan. 2006.
Patel et al., "Involvement of Brca2 in DNA Repair," Molecular Cell, vol. 1, pp. 347-357, Feb. 1998.
Phillips et al., "Epidermal Growth Factor and Hypoxia-induced Expression of CXC Chemokine Receptor 4 on Non-small Cell Lung Cancer Cells is Regulated by the Phosphatidylinositol 3-Kinase/PTEN/AKT/Mammalian Target of Rapamycin Signaling Pathway and Activation of Hypoxia Inducible Factor 1-a," The Journal of Biological Chemistry, vol. 280, No. 23, pp. 22473-22481, Jun. 2005.
Roy et al., "BRCA1 and BRCA2: different roles in a common pathway of genome protection," Nat. Rev. Cancer, vol. 12, No. 1, pp. 68-78, Aug. 2016.
Schneiderman et al., "TTFields alone and in combination with chemotherapeutic agents effectively reduce the viablity of MDR cell sub-lines that over-express ABC transporters," BMC Cancer, vol. 10, No. 229, 2010.
Schultz et al., "p53 Binding Protein 1 (53BP1) is an Early Participant in the Cellular Response to DNA Double-Strand Breaks," The Journal of Cell Biology, vol. 151, pp. 1381-13890, 2000.
Sishc et al., "Telomeres and Telomerase in the Radiation Response: Implications for Instability, Reprogramming, and Carcinogenesis", Frontiers in Oncology, vol. 5, Article 257, Nov. 2015.
Sirbu et al., "Analysis of protein dynamics at active, stalled, and collapsed replication forks," Genes & Development, vol. 25, pp. 1320-1327, 2011.
Stupp et al., "Maintenance Therapy With Tumor-Treating Fields Plus Temozolomide vs. Temozolomide Alone for Glioblastoma—A Randomized Clinical Trial," JAMA, vol. 314, No. 23, pp. 2535-2543, Dec. 2015.
Su et al., "Replication stress induced site-specific phosphorylation targets WRN to the ubiquitin-proteasome pathway," Oncotarget, vol. 7, No. 1, pp. 46-65, Dec. 2015.
Turner et al., "Hallmarks of 'BRCAness' in sporadic cancers," Nature Reviews, vol. 4, pp. 1-6, Oct. 2004.
Venere et al., "Phosphorylation of ATR-Interacting Protein on Ser239 Mediates and Interaction with Breast-Ovarian Cancer Susceptibility 1 and Checkpoint Function," Cancer Res., vol. 67, No. 13, pp. 6100-6105, Jul. 2007.
Voloshin et al., "Alternating electric fields (TTFields) in combination with paclitaxel are therapeutically effective against ovarian cancer cells in vitro and in vivo," International Journal of Cancer, vol. 139, pp. 2850-2858, 2016.
Vymazal et al., "Response Patterns of Recurrent Glioblastomas Treated with Tumor-Treating Fields," Seminars in Oncology, vol. 41, No. 5, pp. S14-S24, Oct. 2014.
Wong et al., "Response assessment of NovoTTF-100A versus best physician's choice chemotherapy in recurrent glioblastoma,"Cancer Medicine, vol. 3, No. 3, pp. 592-602, 2014.
International Search Report and Written Opinion for International Application No. PCT/US2022/020024, mailed Sep. 9, 2022.

Dillon, M. T., Boylan, Z., Smith, D., Guevara, J., Mohammed, K., Peckitt, C., Saunders, M., Banerji, U., Clack, G., Smith, S. A., et al. (2018). PATRIOT: A phase I study to assess the tolerability, safety and biological effects of a specific ataxia telangiectasia and Rad3-related (ATR) inhibitor (AZD6738) as a single agent and in combination with palliative radiation therapy in patients with solid tumours. Clin Transl Rad Onco 12, pp. 16-20.
Franciosi, V., Cocconi, G., Michiara, M., Di Costanzo, F., Fosser, V., Tonato, M., Carlini, P., Boni, C., and Di Sarra, S. (1999). Front-line chemotherapy with cisplatin and etoposide for patients with brain metastases from breast carcinoma, nonsmall cell lung carcinoma, or malignant melanoma: a prospective study. Cancer 85, pp. 1599-1605.
Gaillard, H., Garcia-Muse, T., and Aguilera, A. (2015). Replication stress and cancer. Nat Rev Cancer 15, pp. 276-289.
Militello et al., Mechanism of Action and Clinical Efficacy of CDK4/6 Inhibitors in BRCA-Mutated, Estrogen Receptor-Positive Breast Cancers: Case Report and Literature Review, Frontiers in Oncology, vol. 9, p. 1-7 (Year: 2019).
Knudsen et al., Biological specificity of CDK4/6 inhibitors: dose response relationship, in vivo signaling, and composite response signature, Oncotarget, vol. 8, p. 43678-43691. (Year: 2017).
Karanam, N. K., Srinivasan, K., Ding, L., Sishc, B., Saha, D., and Story, M. D. (2017). Tumor-treating fields elicit a conditional vulnerability to ionizing radiation via the downregulation of BRCA1 signaling and reduced DNA double-strand break repair capacity in non-small cell lung cancer cell lines. Cell Death & Disease 8, e2711, pp. 1-10.
International Search Report and Written Opinion of The International Searching Authority in International Application No. PCT/US2021/023393 dated Jun. 8, 2021, 5 pages.
Kent et al., The broken cycle: E2F dysfunction in cancer, Nature, vol. 19, p. 326-338 (Year: 2019).
Longley, D. B., Harkin, D. P., and Johnston, P. G. (2003). 5-fluorouracil: mechanisms of action and clinical strategies. Nat Rev Cancer 3, pp. 330-338.
Morgensztern, D., Goodgame, B., and Govindan, R. (2010). Vaccines and immunotherapy for non-small cell lung cancer. Journal of Thoracic Oncology : official publication of the International Association for the Study of Lung Cancer 5, pp. S463-S465.
Morgensztern, D., and Govindan, R. (2010). Best of the month: a roundup of articles published in recent months. Journal of Thoracic Oncology : official publication of the International Association for the Study of Lung Cancer 5, pp. 1305-1307.
Pommier, Y., Leo, E., Zhang, H., and Marchand, C. (2010). DNA topoisomerases and their poisoning by anticancer and antibacterial drugs. Chem Biol 17, pp. 421-433.
Schlacher, K., Wu, H., and Jasin, M. (2012). A distinct replication fork protection pathway connects Fanconi anemia tumor suppressors to RAD51-BRCA1/2. Cancer Cell 22, pp. 106-116.
Ulukan, H., and Swaan, P. W. (2002). Camptothecins: a review of their chemotherapeutic potential. Drugs 62, pp. 2039-2057.
Wallez, Y., Dunlop, C. R., Johnson, T. I., Koh, S. B., Fornari, C., Yates, J. W. T., Bernaldo de Quiros Fernandez, S., Lau, A., Richards, F. M., and Jodrell, D. I. (2018). The ATR Inhibitor AZD6738 Synergizes with Gemcitabine In Vitro and In Vivo to Induce Pancreatic Ductal Adenocarcinoma Regression. Mol Cancer Ther 17, pp. 1670-1682.
Wenger, C., Giladi, M., Bomzon, Z., Salvador, R., Basser, P. J., and Miranda, P. C. (2015). Modeling Tumor Treating Fields (TTFields) application in single cells during metaphase and telophase. Conference proceedings : Annual International Conference of the IEEE Engineering in Medicine and Biology Society IEEE Engineering in Medicine and Biology Society Annual Conference 2015, pp. 6892-6895.
Zhang, J., Dai, Q., Park, D., and Deng, X. (2016). Targeting DNA Replication Stress for Cancer Therapy. Genes (Basel) 7, pp. 1-16.
Piezzo et al. Targeting Cell Cycle in Breast Cancer: CDK4/6 Inhibitors, International Journal of Molecular Sciences, vol. 21, p. 1-23. (Year: 2020).
Yuan et al., Selective inhibition of CDK4/6: A safe and effective strategy for developing anticancer drugs, Acta Pharmaceutica SInica B, vol. 11, p. 30-54 (Year: 2021).

(56) References Cited

OTHER PUBLICATIONS https://www.selleckchem.com/products/rgb-286638-free-base.html (Year: 2022).
Kurtyka et al., E2F Inhibition Synergizes with Paclitaxel in Lung Cancer Cell Lines, PLOS ONE, vol. 9, p. 1-9. (Year: 2014).
Examination and Search Report of Taiwan Patent Application No. 110110392 from The Tai E International Patent & Law Office.
International Preliminary Report on Patentability issued in International Application No. PCT/US2023/065242, 9 pages, dated Oct. 3, 2023.
International Preliminary Report on Patentability for International Application No. PCT/US2020/050745, mailed Mar. 24, 2022, 8 Pages.
International Preliminary Report on Patentability for International Application No. PCT/US2021/023393, mailed Oct. 6, 2022, 5 Pages.
Office Action and Search Report from Taiwan Patent Application No. 110110392, dated Oct. 24, 2023, 26 Pages.
Extended European Search Report for Application No. 21774257.6, dated Mar. 20, 2024, 10 Pages.
Office Action from Taiwan Patent Application No. 110110392, dated May 10, 2024, 5 Pages.
Karanam., N. K. et al., "Tumor Treating Fields Cause Replication Stress and Interfere with DNA Replication Fork Maintenance: Implications for Cancer Therapy," Translational Research, 2020, vol. 217, pp. 33-46.
Naz S., et al., "Abemaciclib, a Selective CDK4/6 Inhibitor, Enhances the Radiosensitivity of Non-Small Cell Lung Cancer In Vitro and In Vivo," Clinical Cancer Research, 2018, vol. 24, vol. 16, pp. 3994-4005.
Office Action for Japanese Patent Application No. 2022-558097, mailed May 20, 2025, 12 pages.
Patnaik A., et al., "Efficacy and Safety of Abemaciclib, an Inhibitor of CDK4 and CDK6, for Patients with Breast Cancer, Non-Small Cell Lung Cancer, and Other Solid Tumors," Cancer Discovery, 2016, vol. 6, No. 7, pp. 740-753.

* cited by examiner

TABLE 1

| Cohort | Growth Rate %/week) | Synergy | Synergy p Value |
|---|---|---|---|
| Control | 14.58 | | |
| PD-L1 | 15.99 | | |
| TTFields | 14.17 | | |
| Radiation | 14.07 | | |
| TTFields + PD-L1 | 17.38 | | |
| TTFields + Radiation | 8.71 | + | $2 \times 10^{-4}$ |
| Radiation + PD-L1 | 5.43 | + | $2 \times 10^{-8}$ |
| TTFields + Radiation + PD-L1 | -3.88 | + | $2 \times 10^{-12}$ |

METHODS AND APPARATUS FOR APPLYING TUMOR TREATING FIELDS COMBINED WITH PERSONALIZED ULTRA-FRACTIONATED STEREOTACTIC ADAPTIVE RADIOTHERAPY

CROSS REFERENCE TO RELATED APPLICATIONS

This application claims the benefit of U.S. Provisional Application Ser. No. 63/362,369, filed Apr. 1, 2022, which is incorporated herein by reference in its entirety.

This application is further related to Provisional Application Ser. No. 62/900,166, filed Sep. 13, 2019, PCT/US2020/050745 (WIPO WO2021051089A1), filed Sep. 14, 2020, U.S. application Ser. No. 17/208,107, filed Mar. 22, 2021, U.S. application Ser. No. 17/693,108, filed Mar. 11, 2022, and U.S. application Ser. No. 15/938,088, filed Mar. 28, 2018, which are incorporated herein by reference in their entirety.

BACKGROUND

Tumor treating fields (TTFields) are low intensity alternating electric fields within the intermediate frequency range, which may be used to treat tumors as described in U.S. Pat. No. 7,565,205. TTFields are induced non-invasively into a region of interest by transducers placed directly on the patient's body and applying AC voltages between the transducers. AC voltage is applied between the first pair of transducers for a first interval of time to generate an electric field with field lines generally running in the front-back direction. Then, AC voltage is applied at the same frequency between the second pair of transducers for a second interval of time to generate an electric field with field lines generally running in the right-left direction. The system then repeats this two-step sequence throughout the treatment.

In addition, conventional techniques of radiotherapy treatment for cancer patients have almost exclusively been restricted to fractionated doses of radiation. Fractionated doses, or fractions, are administered within a short time frame, on consecutive days, or even multiple times per day or every other day, over the course of a few weeks. This is known as conventional fractionated radiotherapy (CFRT). In this timeframe, a patient would receive daily or near-daily doses of radiation. The radiation is typically administered with a linear accelerator and is used to control or kill malignant cells that make up a tumor.

Various attempts at applying split-course treatments of radiotherapy have been attempted, but never to the point of success. Split-course treatment is an intentional separation or spreading out of radiation doses. In the past, the split or rest period occurred between clusters of fractionated doses, e.g., at the half-way point of a 6-week course, a 1-4 week break with no therapy was inserted. Historically, the motivation for this was to reduce toxicity, allowing more time for the normal tissue surrounding the tumor to heal from what would otherwise be a difficult and toxic long course of radiation. However, tumor control penalties caused by tumor proliferation plagued these attempts, meaning that, with the extra time between doses, the tumor would begin to grow back.

As a result, radiotherapy treatments in general tend to be very rigid and do not allow for much adaptation or personalization. It is not uncommon for the only customization in radiotherapies to be based on the type and location of the tumor determined prior to the onset of therapy. For example, a patient with primary lung cancer may be put on a treatment sequence consisting of 30 fractions of 2 Gy (Gray) ionizing radiation over 6 weeks, while a patient with metastatic kidney cancer may receive 5 fractions of 8 Gy every other day over 2 weeks. However, there is little customization or adaptation, such as narrowing the radiation field because of a shrinkage in tumor size, beyond that. Since little real change occurs throughout the course of conventional therapy, the entire course is planned prior to the start of all therapy and executed without modification or adaptation. Because of this rigidity, there can be a tendency for patients to be either over or under-treated. Furthermore, even if adaptation is implemented, there is little time for the tumor or its environment to demonstrate notable or noticeable changes that might influence adaptations or personalization with such a short amount of time between fractions and completion of all radiotherapy typically within 4-6 weeks total.

SUMMARY

As will be discussed in more detail below, the following novel methods and apparatuses involve, in some respects, the combination of TTFields with a radiation delivery regimen referred to as Personalized Ultra-fractionated Adaptive Radiotherapy (PULSAR). PULSAR is an ablative and adaptive approach to radiotherapy. Ablative strategies like Stereotactic Ablative Radiotherapy (SAbR) are now common in radiation oncology, in an increasing number of treatment settings. Conventional, ablative treatments such as SAbR involve radiotherapy wherein numerous fractions of radiation are delivered over weeks or days. However, PULSAR bears no relation to conventional treatments and instead introduces radiation pulses at far longer intervals than that of conventional radiotherapy or SAbR, the radiation treatments are referred to as pulses. As an improvement over conventional approaches, applying treatment in pulses over customized time interval is highly effective in combination with the application of TTFields, or in combination with the application of TTFields along with a specific chemotherapy agents and immune checkpoint inhibitors. Indeed, PULSAR therapy is adaptable to the tumor, tumor microenvironment, and normal tissue response to the therapy, such that treatment can be modified to in response to a patient's clinical circumstances.

In addition to the effectiveness of PULSAR, TTFields are also effective in that they create conditional vulnerabilities to agents (e.g., ionizing radiation) that damage DNA. Clinical data created in furtherance of this novel combinatorial therapy, demonstrates that dramatic radiosensitization in subcutaneously growing tumors in immunocompetent subjects (e.g., mice). As will be discussed below, since PULSAR relies on extended periods of time between radiation "pulses" (e.g., intervals of time never used or considered conventional radiotherapy), in some instances TTFields is applied within those periods of time. Furthermore, other agents that cause DNA damage, inhibit DNA replication fork progress or maintenance, or cause DNA replication fork collapse additionally applied during the time intervals in between pulses. Moreover, because TTFields triggers a innate immune response via a blockade of mitophagy, and high dose radiation exposure like those used in PULSAR will do the same, there is every indication to combine PULSAR and TTFields with immune oncology approaches like immune checkpoint inhibition.

One aspect of the invention is directed to a method of treating a tumor in a subject, the method comprises: applying a tumor treating field to the tumor at a frequency between approximately 80 KHz and approximately 300 kHz; and delivering an ablative, adaptive, and novel Personalized Ultra-fractionated Adaptive Radiotherapy (PULSAR) regimen.

One aspect of the invention is directed to a method of treating a tumor in a subject, comprising: applying a tumor treating field to the tumor at a frequency between approximately 80 kHz and approximately 300 kHz; delivering an ablative, adaptive, and novel Personalized Ultra-fractionated Adaptive Radiotherapy (PULSAR) regimen; and delivering agents that cause DNA damage, inhibit DNA replication fork progress or maintenance, or cause DNA replication fork collapse in the interim between pulses.

In yet another aspect of the invention, a method may include applying a tumor treating field to the tumor at a frequency between approximately 80 KHz and approximately 300 kHz; administering a first pulse dose of radiation to a tumor within a subject; measuring biologic features of at least one of the subjects and the tumor.

DESCRIPTION OF EMBODIMENTS

Techniques for treating a tumor in a subject are disclosed. The present disclosure relates to Tumor Treating Fields (TTFields) delivered in combination with Personalized Ultra-fractionated Adaptive Radiotherapy (PULSAR), which when applied in a regimen, may induce synergistic cell killing via the disruption of DNA damage response, enhanced DNA replication stress and DNA replication fork collapse.

The disclosed TTFields can reduce tumor cells through the disruption of mitosis. Furthermore, the disclosed TTFields can affect DNA damage repair and replication stress pathways of tumor cells. For example, the disclosed TTFields treatment can decrease Fanconi Anemia (FA) pathway signaling proteins by impairing irradiation (IR)-induced DNA damage repair processes. The length of newly replicated DNA can be slowed as a function of TTFields exposure time, and TTFields can increase R-loop formation, which indicates that TTFields induced replication stress. The disclosed TTFields can increase the sensitivity of chemotherapy agents that target and increase replication stress in novel combination therapy options.

Ablative strategies like Stereotactic Ablative Radiotherapy (SAbR) are now common in radiation oncology, in an increasing number of treatment settings. However, PULSAR bears no relation to conventional radiotherapy where numerous "fractions" of radiation were delivered over weeks rather than in days (SAbR) or in weeks or months now with PULSAR, and because the interval between radiation fractions is far longer than that of conventional radiotherapy or SAbR, the radiation treatments are referred to as pulses. This interval in pulses is highly appropriate for the application of TTFields or TTFields plus specific chemotherapy agents and immune checkpoint inhibitors. As PULSAR was developed with the intent of integrating both the tumor, tumor microenvironment, and normal tissue response to therapy it is primed for integration of additional innovations in response to a patient's clinical circumstances.

Figure 1:
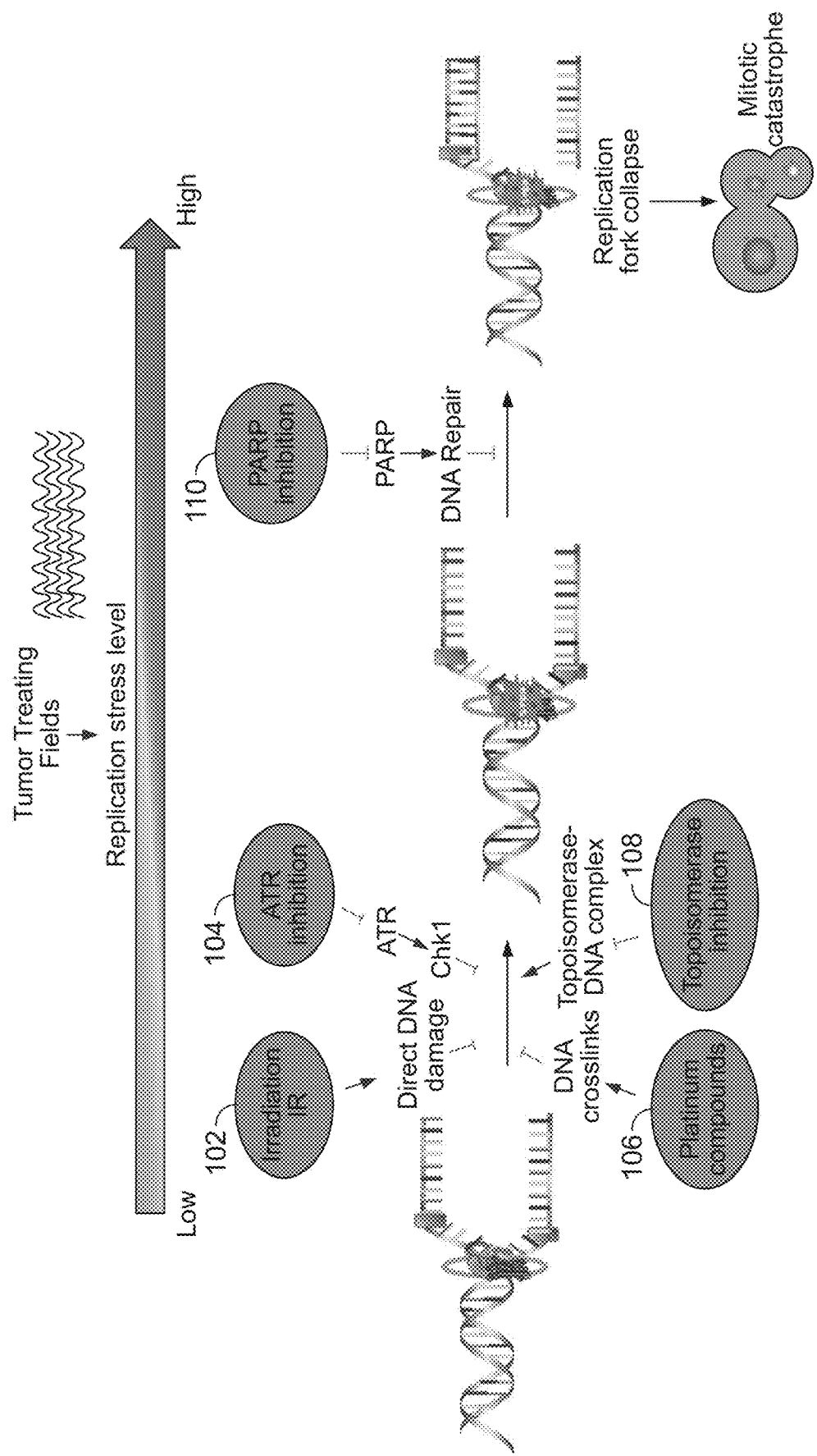
FIG. 1 depicts example approaches for treating a tumor in a subject in accordance with exemplary embodiments of the present disclosure.

FIG. 1 depicts example inventive approaches for treating a tumor in a subject in accordance with exemplary embodiments of the present disclosure. Each of these inhibitors may target, for example, DNA repair, DNA replication, DNA crosslinks, DNA complex, or cell cycle regulation in order to increase replication stress. For example, ATR inhibitors 104 (an agent that blocks a key DNA repair protein) may be introduced to tumor cells or tissue for inhibiting the cell cycle checkpoint upon DNA damages. Irradiation (IR) 102 (a process by which an object is exposed to radiation) can be applied to the tumor cell or tissue for breaking DNA strands. Platinum agents 106 (a substance that binds DNA nucleotides together and blocks DNA synthesis) can be delivered to the tumor cell or tissue for inducing intra-strand cross-links that can inhibit DNA replication. Repair of crosslinks can be downregulated by TTFields. PARP inhibitors 110 (inhibitors stop the PARP from implementing cellular repair processes) can be applied to tumor cells or tissue for the inhibition of replication fork maintenance. Topoisomerase inhibitors 108 (a class of enzymes that alter the supercoiling of double-stranded DNA) can be delivered to tumor cells or tissue for the inhibition of DNA replication and chromosome condensation.

The disclosed combination therapy options using chemotherapeutic agents can synergistically increase replication stress in combination with TTFields. The disclosed chemotherapeutic agents can target replication stress, which can be the primary cause of genome instability. Cancer cells can maintain unrestrained proliferation by keeping low to mild levels of replication stress with defective DNA damage response (DDR) and loss of cell cycle checkpoints. Normal cells can maintain genome stability through the coordinated actions of DDR and cell cycle checkpoints. Defects in DDR and mild to low levels of replication stress are unique to cancer cells and, therefore, can be therapeutically exploited. To exploit replication stress, the disclosed TTFields can be combined with the disclosed chemotherapeutic agents, which can also cause replication stress at several key steps.

Figure 2:
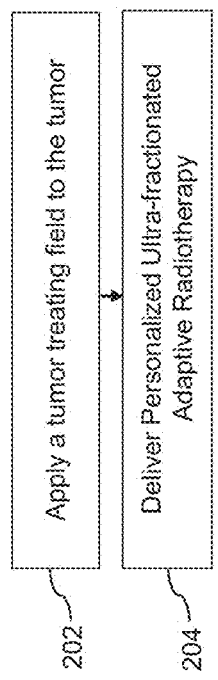
FIG. 2 depicts an example method of treating a tumor in a subject, in accordance with exemplary embodiments of the present disclosure.

FIG. 2 depicts an example method 200 of treating a tumor in a subject. At 206, tumor treating fields (TTFields) can be applied to the tumor. In non-limiting embodiments, the TTFields can be applied with predetermined parameters. As an example, the TTFields can include a frequency within a frequency range from about 50 KHz to about 1000 kHz. As an example, the frequency of the tumor treating field may be between approximately 200 kHZ and approximately 500 kHZ. As an example, the frequency of the tumor treating field may be approximately 100 kHZ, approximately 150 kHZ, approximately 200 kHZ, or approximately 250 kHZ. As an example, the TTFields may include an intensity within an intensity range from about 1 V/cm to about 20 V/cm. As an example, the TTFields may include an intensity within an intensity range from about 1 V/cm to about 10 V/cm. As an example, the intensity of the tumor treating field may be between approximately 1 V/cm and approximately 4 V/cm. Other possible exemplary parameters for the TTFields may include active time, dimming time, and duty cycle (all of which may be measured in, for example, ms units), among other parameters. The parameters can be modified based on the sizes of tumor, types of tumors, subjects, or purposes of the treatment. In one example, the intensity of the tumor treating field is between approximately 1 V/cm and approximately 4 V/cm, and the frequency of the tumor treating field is between approximately 150 kHZ and approximately 250 kHZ for treating glioblastoma cancer cells.

The disclosed TTFields treatment can induce DNA damage, impair DNA damage response, and create conditional vulnerabilities. The application of the disclosed TTFields can increase in γ-H2AX foci with time in cells (e.g., that were not irradiated but were exposed to TTFields). Because γ-H2AX is also an early sensor of stalled replication forks during replication stress, TTFields exposure can induce replication stress, as reduced expression of BRCA1 and other members of the Fanconi Anemia pathway, negatively affects the repair of collapsed or stalled replication forks. Furthermore, the MCM6 and MCM10 genes, integral members of the DNA replication complex, can also be downregulated by the application of the TTFields.

In certain embodiments, the TTFields can be applied to the tumor before or after the disclosed inhibitors and/or PULSAR therapy is applied. In certain embodiments, the TTFields can be simultaneously applied to the target tissue with the disclosed inhibitors and/or PULSAR therapy. As an example, the TTFields may be applied to the tumor before the PULSAR therapy to set up a conditional vulnerability that cause the impaired cells to become more vulnerable to the PULSAR therapy. However, alternatively, at least a portion of the applying step 202 may be performed simultaneously/concomitantly with at least a portion of the delivering step 202 and/or at least a portion of 204. In non-limiting embodiments, the disclosed agents/inhibitors can be delivered concomitant with TTFields and/or PULSAR therapy. As an example, at least a portion of the applying step 204 may be performed simultaneously with at least a portion of the delivering step 202. In certain embodiments, the fluctuation in weight of the subject may server as a condition for transitioning form treatment with the TTFields at 202 to beginning the PULSAR regimen at 204. In addition, in one non-limiting embodiment, TTFields may be applied for a predetermined period of time (e.g., approximately 7 days), followed by a rest period for a predetermined period of time (e.g., approximately 3 days). Alternatively, TTFields may be applied continually throughout the regimen alongside the delivery of PULSAR at 204, At 204, PULSAR can be delivered to the tumor. In one example, a first test dose of radiation, called the first pulse, may be administered to a tumor within a subject. The tumor may be either benign or malignant. In all embodiments, the dose may be substantial enough to initiate changes in the tumor, tumor environment, or within the patient better facilitating adaptation and personalization. To this end, the pulse dose may be at least 6-8 Gy, possibly more. In some embodiments, the dose may be ablative, defined as disrupting both proliferative capacity and cellular function, and used conventionally as standalone therapy for both primary cancers and metastases. Such doses range from 15-50 Gy per treatment. Often, ablative dose range causes widespread tumor death. For example, the dose may be a dose similar to or the same as a dose that would be applied in stereotactic ablative radiotherapy (SABR). Doses currently used for the first or only fraction in existing SABR treatments for solid tumors range from 8-50 Gy. For example, the dose may be applied with high accuracy and precision and intentionally limited to the gross tumor/cancer, which may mitigate the effects of radiation to normal tissue surrounding the tumor.

Notably, PULSAR is an adaptive regimen that is meant be modified based on the efficacy of treatment and tailored to the specific subject. Accordingly, a second application of TTFields may administered to the subject followed by a second pulse dose of radiation (or more) may be administered to the subject. In some embodiments, the period of time (i.e., rest/observation period) between the first and second doses of radiation may be at least 6-7 days or more. For example, a first dose of 10 Gy may be administered and, 10 days later, a second dose of 10 Gy may be administered. In some embodiments, the rest/observation period may be 10 days, 20 days, 30 days, or even months long. In some embodiments, the second dose may also be ablative and similar to or the same as a dose that would be applied in stereotactic ablative radiotherapy. The second dose may have the same or different potency targeting a larger or smaller target field as the first dose. In some embodiments, the second and subsequent pulse dose levels may be modified or adapted based on information obtained during the rest/observation period or periods.

For example, the adaptation impacting the second pulse dose level may be so simple as reducing the dose if the tumor shrinks dramatically after the first pulse. Conversely, the second pulse dose may be larger than the first if the tumor failed to respond or even grew after the first pulse. When tumors respond after the first or any previous pulse, the next planned pulse may treat the smaller volume as an adaptation. Another example may be that the previous pulse caused new hypoxia based on imaging that constitutes focal radio resistance. In response, an additional dose may be "painted" using dosimetric modulation to these hypoxic areas when planning the upcoming pulse. In response, a hypoxic cell sensitizing drug may be given in addition to the next radiation pulse.

Another example might be that sampling of circulating tumor cells or repeat biopsy or other laboratory or imaging changes indicate that the targeted tumor(s) might benefit from the addition of a specific class of drugs, targeted therapy, or immunotherapy. In this circumstance, the subsequent pulse might be delivered along with this drug or combination treatment in a fashion that is known to optimize the combination. Another example may be that the tumor response indicates that radiation alone will never eliminate the patient's particular tumor. In this circumstance, the patient may be referred for surgery or drug therapy without radiation. The process of providing pulses of dose in this fashion may be repeated either until the cancer is eliminated (cured), the treatment causes unacceptable toxicity, or until tumor progression occurs despite all adaptive options/opportunities being exhausted.

In some embodiments, prior to performing 204 and administering the second dose of radiation to the subject with a tumor, a level of radiation or potency, duration of the rest/observation period, and target field for the second dose may be determined. For example, a treatment may be personalized and adapted for a specific patient based on their response to an initial dose of radiation. The patient's response to the initial dose may encompass a wide variety of factors including, but not limited to, symptoms, exams, imaging, tumor response, blood tests, bodily fluid analysis, biopsies, histology, grade, stage, genomics, sequencing, gene expression, performance, patient tolerance, attitude, social circumstances, or any other personal test. Because the rest/observation period between doses is relatively long, meaning not on back-to-back days and ideally more than seven days, there is ample time for the patient's body and the tumor to adapt. For example, if a tumor is determined to have characteristics that suggest a high risk for rapid growth, the rest period between doses may be shorter than when tumor shrinkage has been detected. Furthermore, extra time between pulses may allow immune cascades to run their designed course throughout the body, making subsequent pulses more effective.

In some embodiments, radiomic and biologic features may be analyzed to further adapt the treatment. Biologic features may include target tissue vascularity, normal tissue vascularity, target tissue oxygenation status, normal tissue oxygenation status, target tissue cytokine profile, normal tissue cytokine profile, target tissue gene expression, normal tissue gene expression, target tissue receptor expression, normal tissue receptor expression, target tissue white blood cell infiltration, normal tissue white blood cell infiltration, tumor markers, tumor burden, systemic immune status, changes in subject health, and changes in patient weight.

In some embodiments, a DNA replication stress inducing agent is delivered to the tumor. A DNA replication stress inducing agent comprises at least one of a platinum compound, an alkylating agent, a wee1 inhibitor, a Chk1 inhibitor, a thymidylate synthase inhibitor, a ribonucleotide reductase inhibitor, Topoisomerase I inhibitor, Topoisomerase II inhibitor, a maternal embryonic leucine zipper kinase (MELK) inhibitor, or a NEDD8-activating enzyme (NAE) inhibitor.

In some embodiments, radiomic features may include features extracted from, or images from, anatomical imaging characteristics (e.g., tumor response, tumor infiltration, edge features, density features, shape features, etc.), functional imaging characteristics (e.g., blood flow, enhancement, etc.), and metabolic imaging characteristics (e.g., glucose uptake, proliferation, hypoxia, etc.).

Using certain embodiments disclosed herein, TTFields in combination with PULSAR, and various were applied to tumors.

EXPERIMENTAL RESULTS

Figure 3:
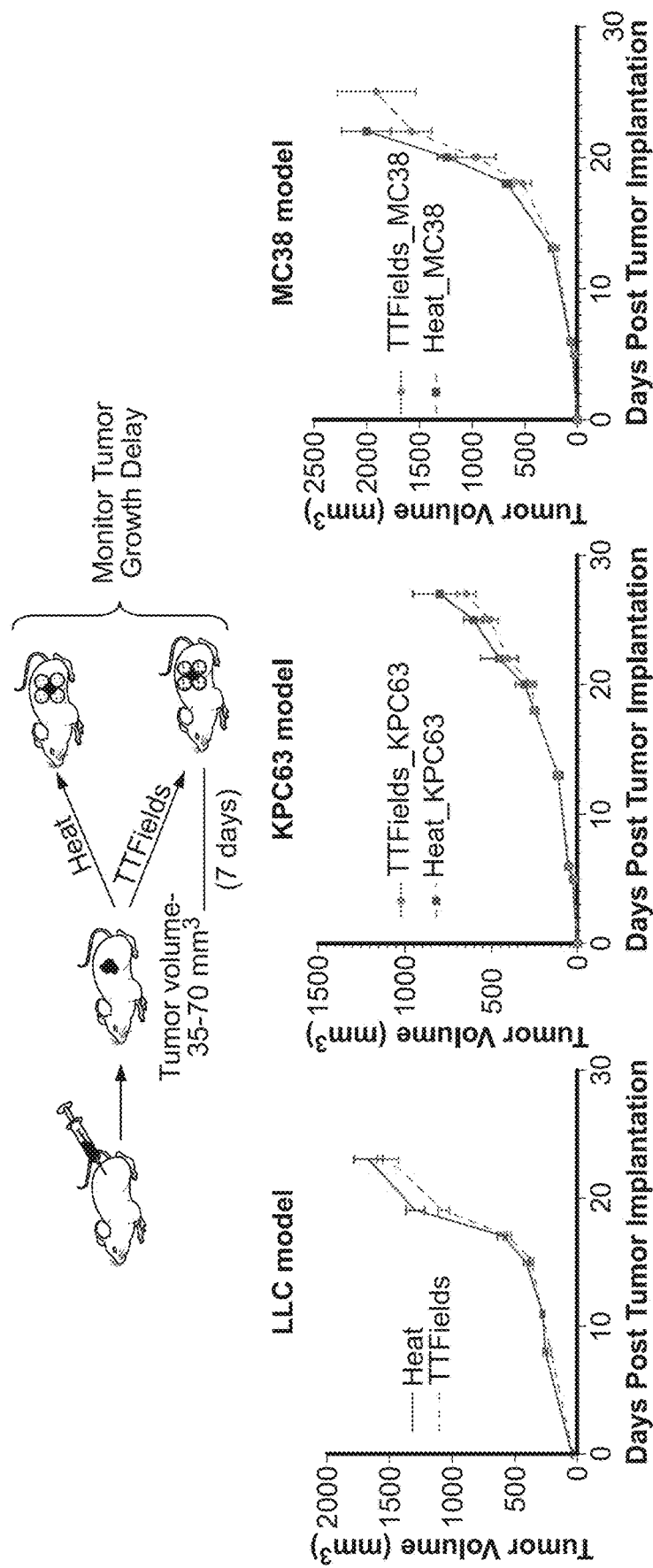
FIG. 3 depicts example effects of TTFields on a subject, in accordance with exemplary embodiments of the present disclosure.

For example, FIG. 3 depicts an example method of treating a tumor in a subject, in accordance with exemplary embodiments of the present disclosure. Tumor growth delay (TGD) experiments were carried out in three different mouse tumor models treated with TTFields. TTFields exposure alone (7 days of continuous exposure) did not decrease the rate of tumor growth in two of the three mouse tumor models with any statistical significance while the MC38 tumor was slower when exposed to TTFields. TTFields treatment did reduce mouse body weight by 7-16% after 7 days of treatment, but the mice quickly regained their weight within 2 days of being moved back to regular cages. Radiation, delivered as a single dose of 8 Gy, was then added to the treatment regimen for the MC38 tumor at the end of the TTFields exposure. Here, after one round of TTFields followed by a single dose of radiation there was a significant delay in tumor growth.

In the next step two rounds of TTFields and radiation were applied. This is a PULSAR treatment strategy where there is a significant gap in treatment times. Tumor growth delay was far more pronounced after two rounds of treatment compared to one. Radiation, delivered as a single dose of 8 Gy, was then added to the treatment regimen for the MC38 tumor at the end of the TTFields exposure. Here after one round of TTFields followed by a single dose of radiation there was a significant delay in tumor growth.

In the next step two rounds TTFields and radiation were applied. This is a PULSAR treatment strategy where there is a significant gap in treatment times. Tumor growth delay was far more pronounced after two rounds of treatment compared to one.

Figure 4A:
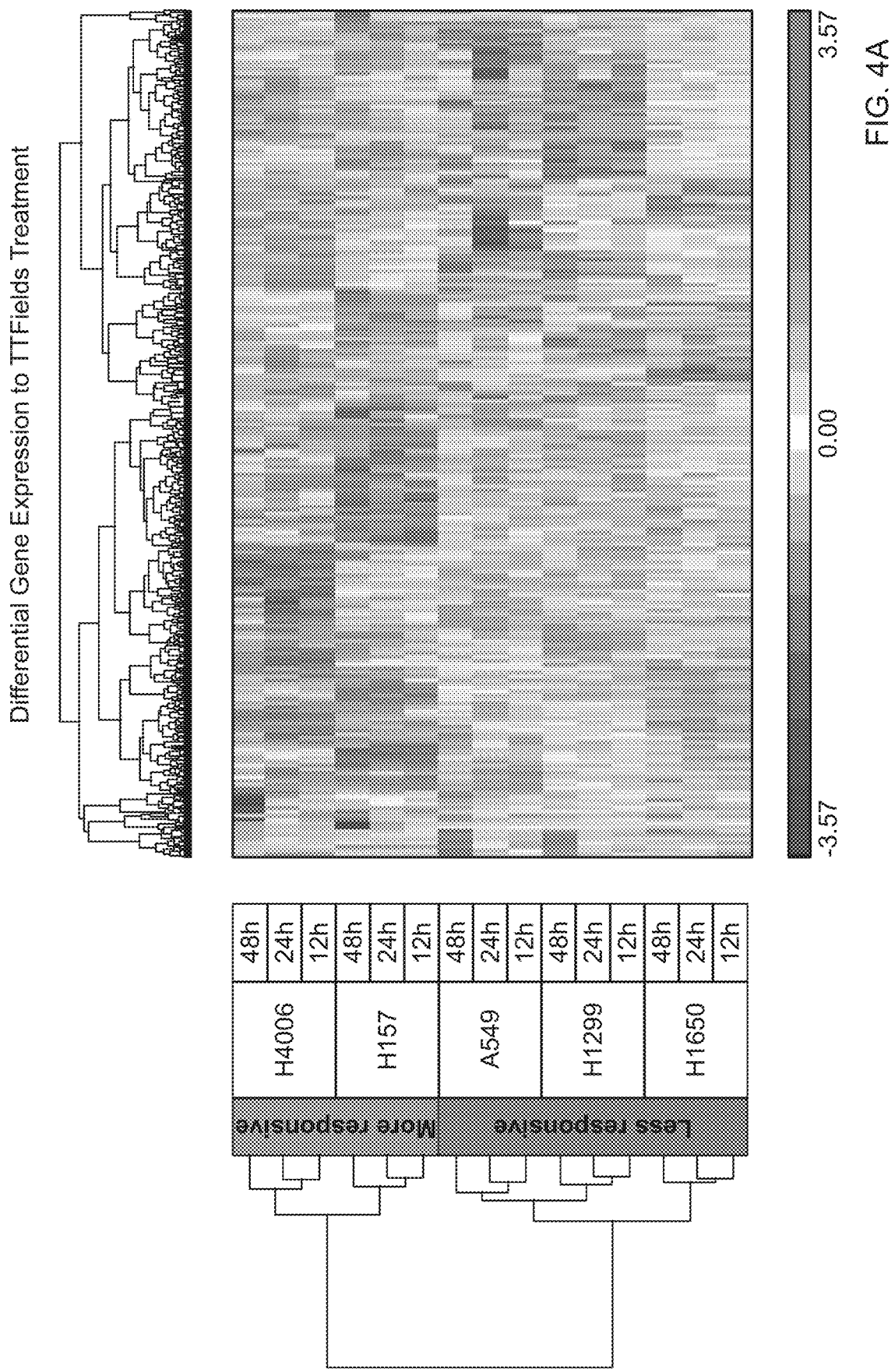
FIG. 4A depicts example effects of TTFields on genes, in accordance with exemplary embodiments of the present disclosure.
Figure 4B:
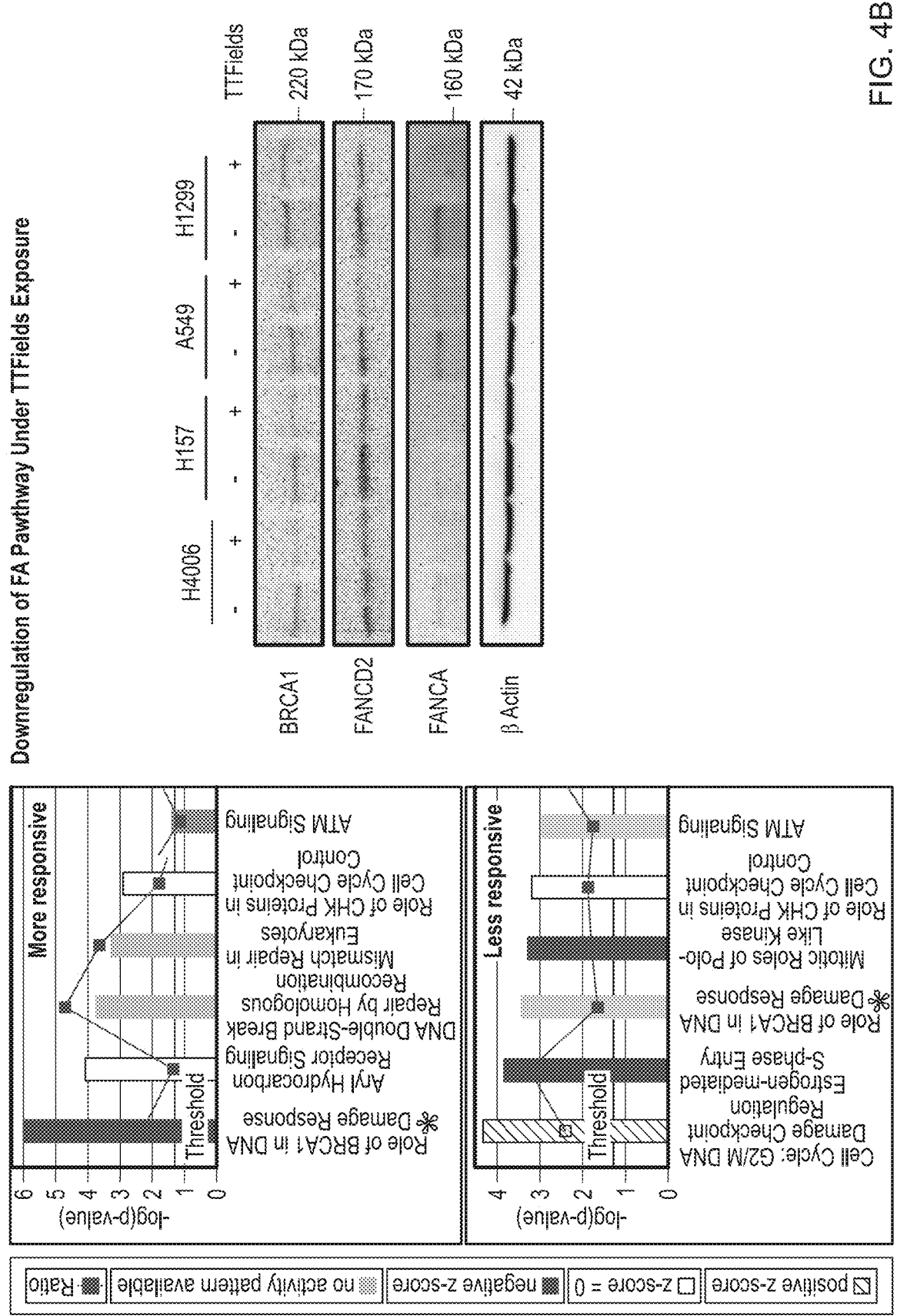
FIG. 4B depicts example effects of TTFields on a Fanconi Anemia pathway, in accordance with exemplary embodiments of the present disclosure.
Figure 4C:
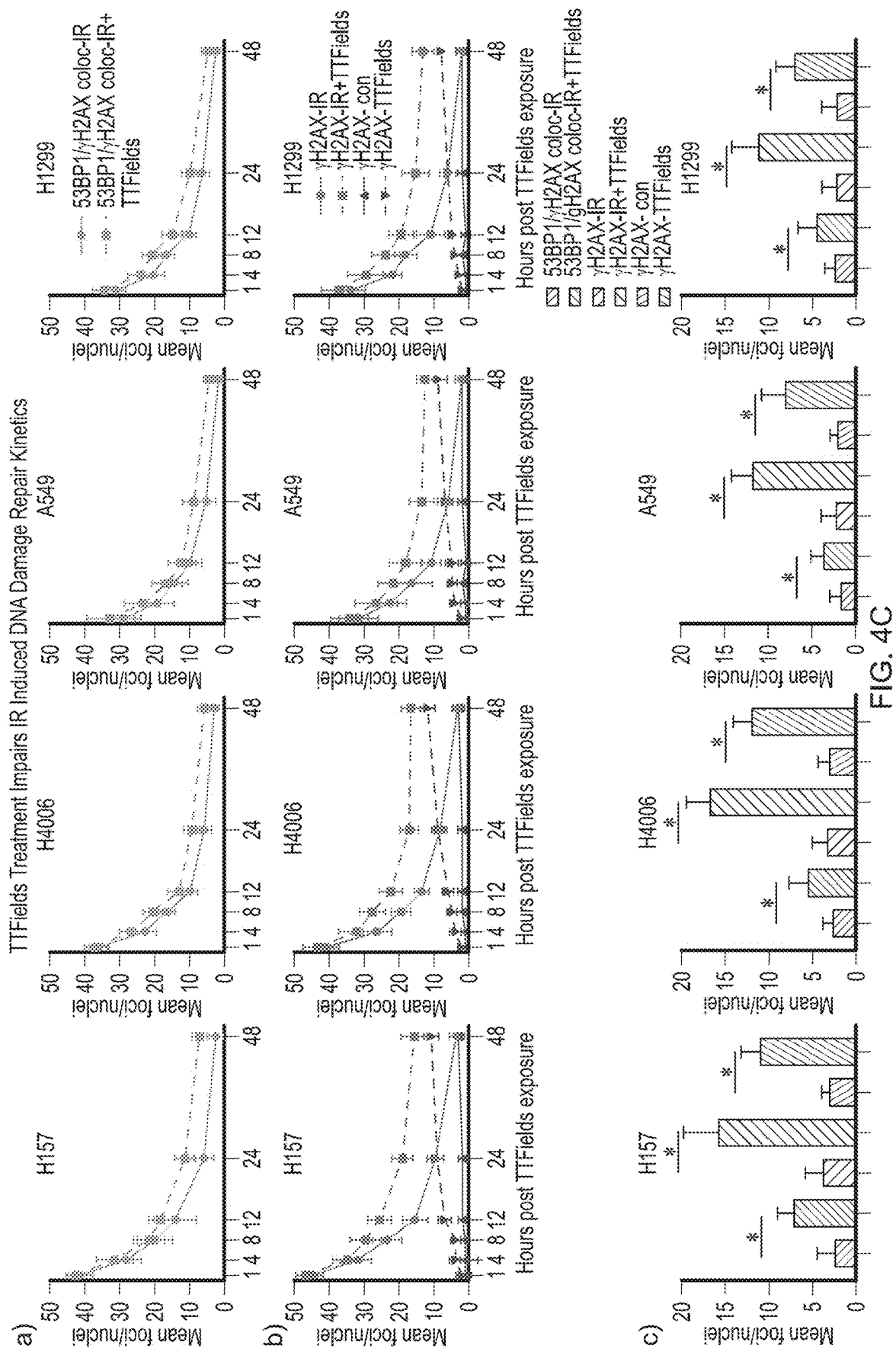
FIG. 4C depicts example effects of TTFields and irradiation on DNA repair kinetics, in accordance with exemplary embodiments of the present disclosure.
Figure 4D:
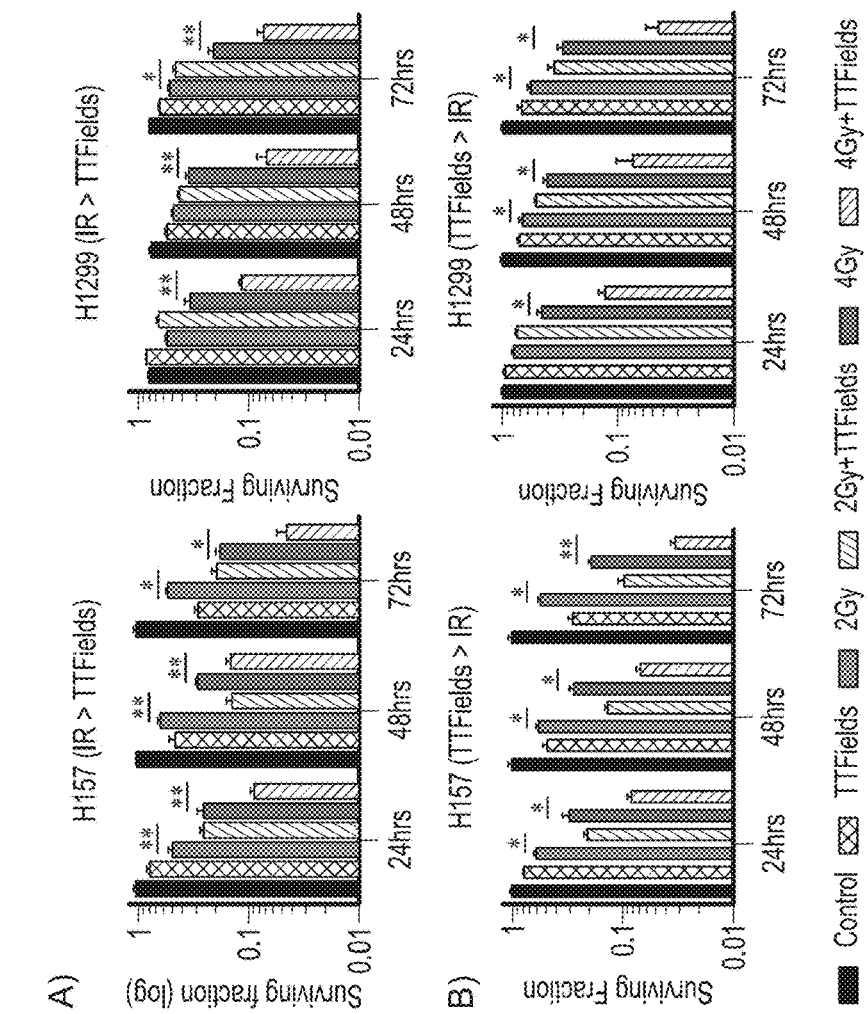
FIG. 4D depicts example effects of TTFields on cells, in accordance with exemplary embodiments of the present disclosure.

FIGS. 4A-4D depicts example effects of TTFields on various subjects. In particular, FIG. 4A depicts a genome expression analysis that was performed using microarrays using panel of NSCLC cells. FIG. 4B depicts downregulation of Fanconi Anemia (FA) pathway under TTFields exposure. From microarray results it was found that BRCA1 DNA damage response pathway genes are downregulated upon TTFields exposure besides cell cycle related defects which is already known. In addition, some FA pathway proteins downregulation was confirmed by western blot. Based on established role of FA pathway plays in DNA damage response an IR induced DNA damage repair kinetics experiment was conducted, which yielded results that, as depicted in FIG. 4C, indicated that TTFields exposure impairs IR induced DNA damage response. Moreover, some experiments demonstrated that TTFields treatment alone induces some degree of DNA double strand breaks which is evident by increased g-H2AX foci. As discussed above, TTFields interfere with DNA damage repair kinetics hypothesized that in a novel combination therapy option of using TTFields together with radiation, TTFields treatment increases IR induced cell death. As depicted in FIG. 4D, the results of some experiments indicated that TTFields increases IR induced cell killing more than additively. Given these findings, an experiment was conducted wherein TTFields were applied to the subject prior to radiation, which yielded results that further indicated that TTFields enhance the sensitivity of radiation which is evident by increased CI values.

Figure 5:
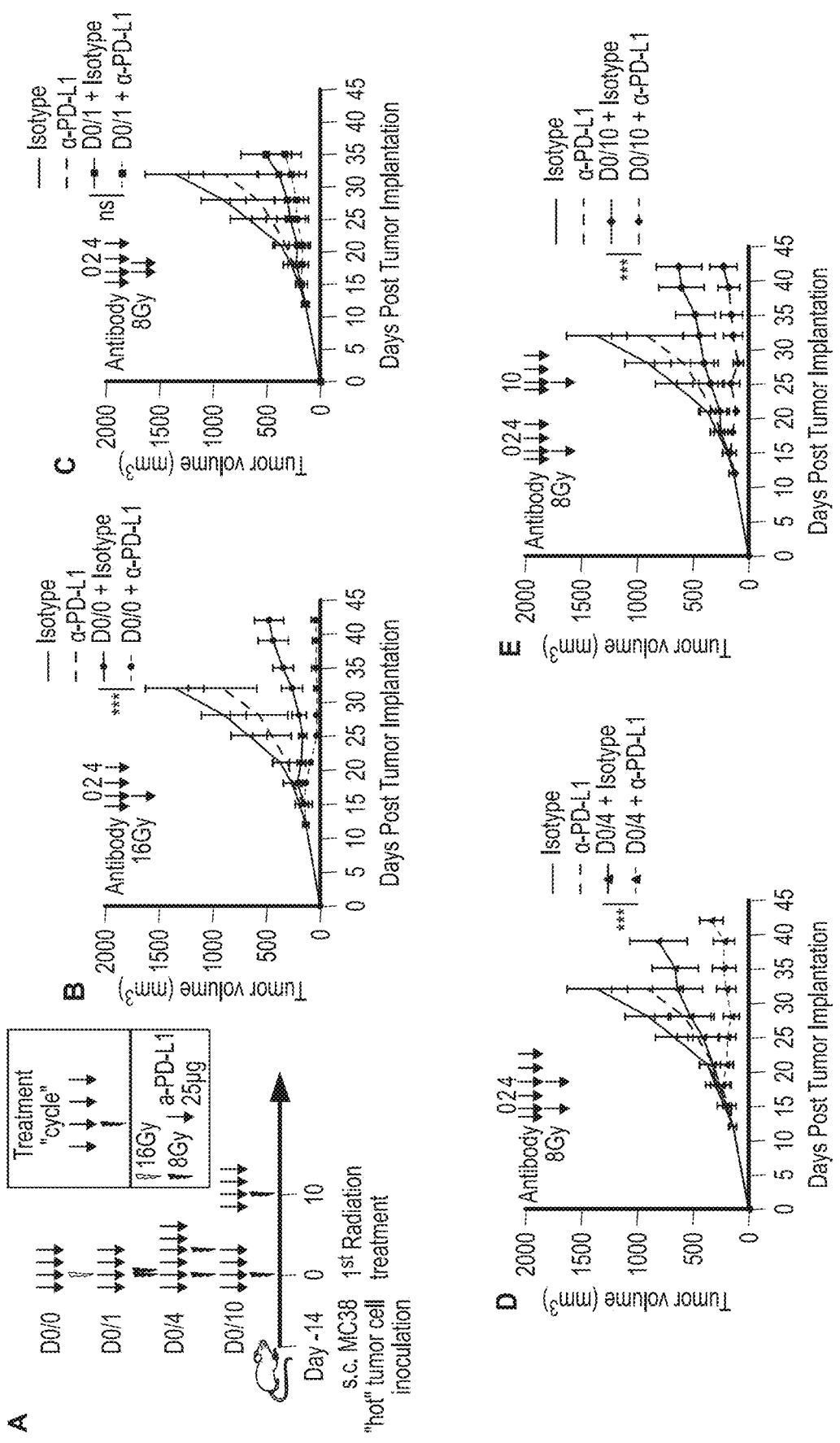
FIG. 5 depicts example effects of radio-immunotherapy pulses in a hot tumor microenvironment, in accordance with exemplary embodiments of the present disclosure.

FIG. 5 depicts example effects of radio-immunotherapy pulses in a hot tumor microenvironment, according to one or more embodiments. For example, FIG. 5 depicts the timing of radio-immunotherapy pulses effects tumor growth in a "Hot" tumor microenvironment utilizing MC38 Cells.

Figure 6:
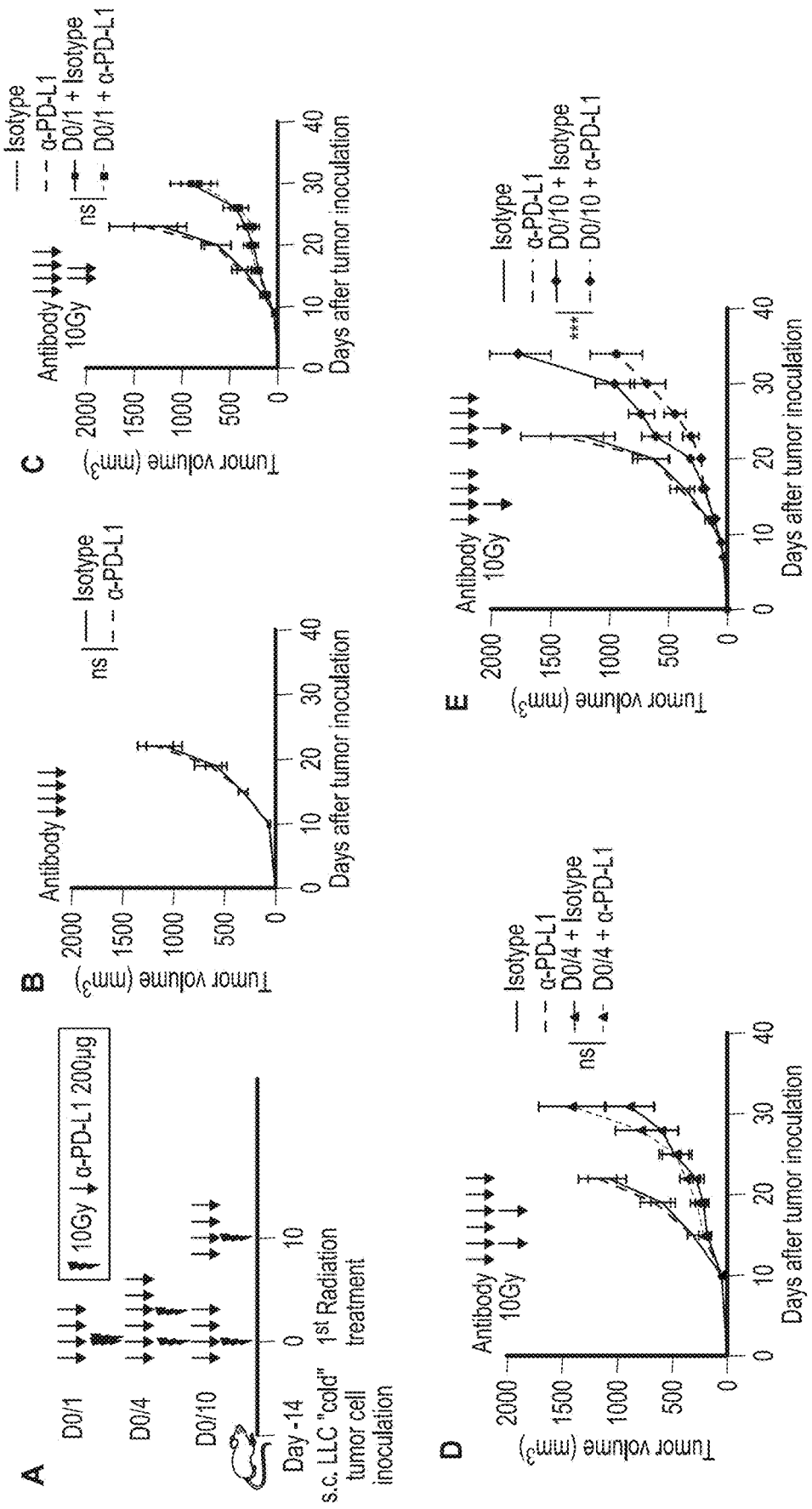
FIG. 6 depicts example effects of radio-immunotherapy pulses in a cold tumor microenvironment, in accordance with exemplary embodiments of the present disclosure.

FIG. 6 depicts example effects of radio-immunotherapy pulses in a cold tumor microenvironment, in accordance with exemplary embodiments of the present disclosure. For example, FIG. 6 depicts the timing of radio-immunotherapy pulses effects tumor growth in a "Cold" tumor microenvironment.

Figure 7:
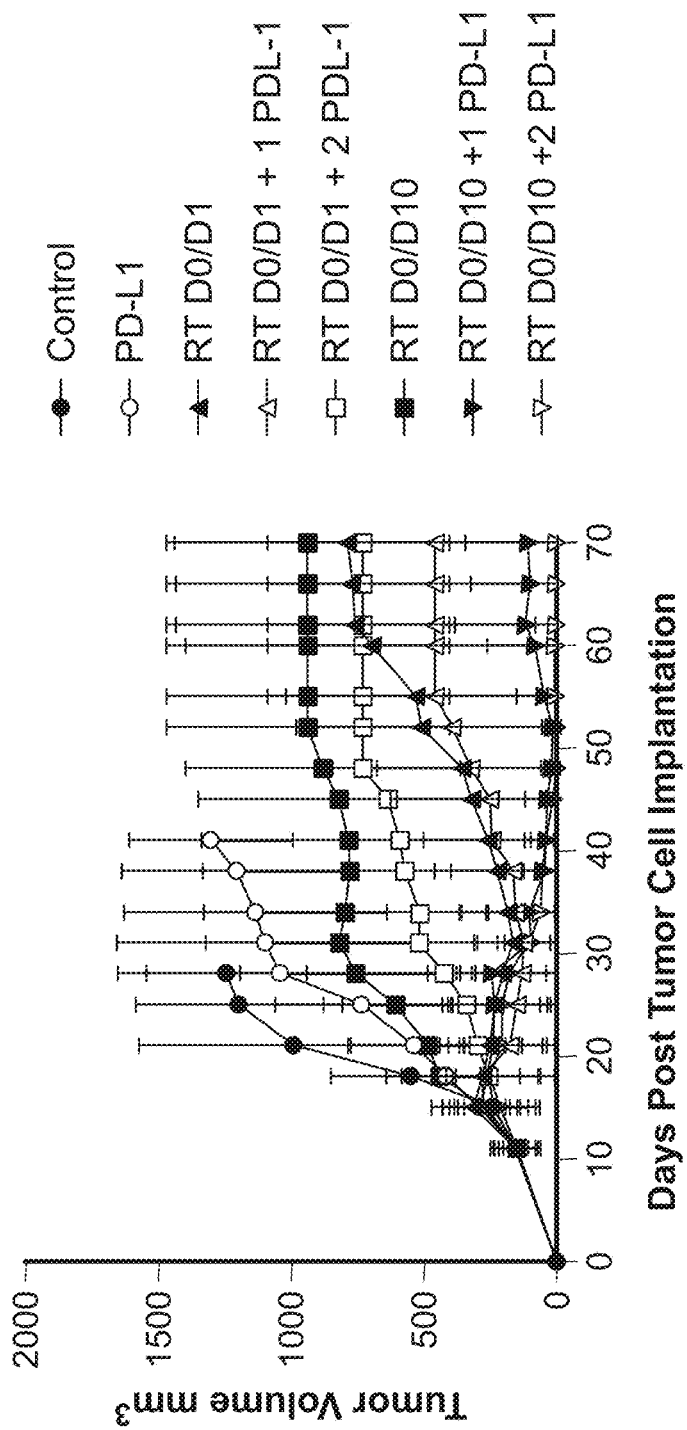
FIG. 7 depicts example effects of PULSAR and immunotherapy on cancer, in accordance with exemplary embodiments of the present disclosure.

FIG. 7 depicts example effects of PULSAR and immunotherapy on cancer, in accordance with exemplary embodiments of the present disclosure. For example, FIG. 7 depicts the effects of PULSAR and Immunotherapy effect on mouse rectal cancer.

Figure 8:
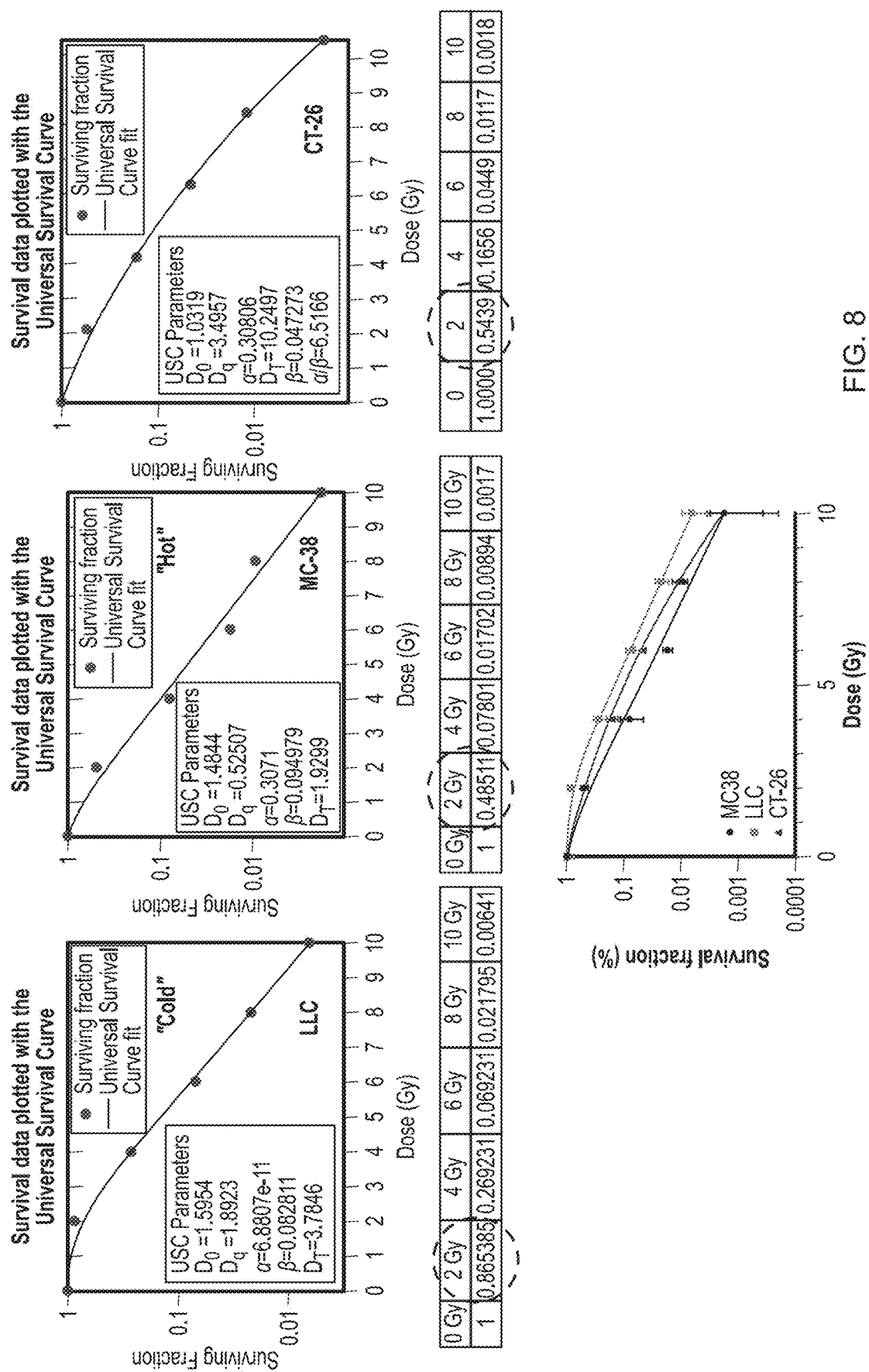
FIG. 8 depicts example survival results in tumor microenvironments, in accordance with exemplary embodiments of the present disclosure.

FIG. 8 depicts example survival results in tumor microenvironments, in accordance with exemplary embodiments of the present disclosure. For example, FIG. 8 depicts survivability data across hot and cold microenvironments. Given that TTFields induce conditional vulnerabilities, experiments were conducted with TTFields in combination therapies. In one experiment, an application of Tumor growth delay (TGD) was applied in combination with radiation. In this experiment, one round of TTFields and IR treatment cycle was used. The results of this TGD approach suggests significant tumor growth delay between TTFields and heat groups in MC38 mouse model after one round of TTFields plus IR treatment: TTFields and heat treatments were started when the tumor volumes reached average volume of 40 mm$^3$. After 7 days of treatment (TTFields or Heat) mice were exposed to 8 Gy radiation. After radiation mice were transferred to regular cages and tumor volumes and body weights were measured every alternative day. TTFields treatment slowed the tumor growth but the significant tumor growth inhibition was observed in TTFields plus IR group mice compared to their controls. In this graph historical controls were used from other study where exact amount of MC38 cells were injected in C57BL/6 and TGD was monitored.

Figure 9:
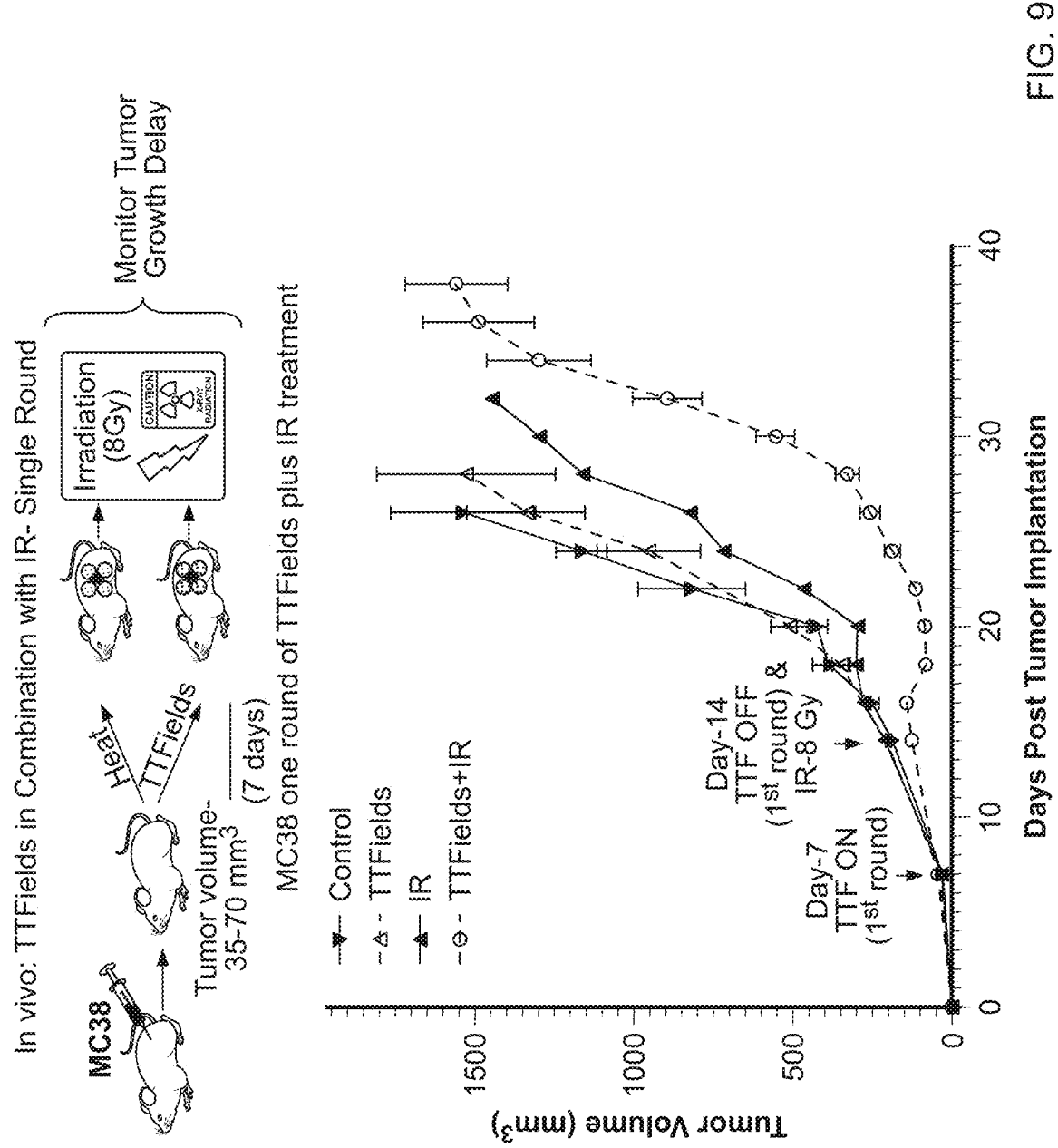
FIG. 9 depicts example effects of a combination of TTFields and irradiation in a single round, in accordance with exemplary embodiments of the present disclosure.

FIG. 9 depicts example effects of a combination of TTFields and irradiation in a single round, in accordance with exemplary embodiments of the present disclosure. For example, in furtherance of the experiment discussed as it relates to FIG. 8, FIG. 9 depicts the results of an experiment using one cycle of TTFields and Radiation treatment combination. For example, TTFields and heat treatments were started when the tumor volumes reached average volume around 40 mm$^3$. After 7 days of treatment (TTFields or Heat) mice were exposed to 8 Gy radiation and mice were allowed to gain body weight in regular cages for 3 days. After 3 days second round of 7 days of treatment (TTFields or Heat) was given to mice and then exposed to 8 Gy radiation. Immediately after second round of Irradiation mice were transferred to regular cages and tumor volumes and body weights were measured every alternative day. One round of TTFields and IR treatment slowed the tumor growth, but the further significant tumor growth inhibition was observed in two rounds of TTFields plus IR treated group mice compared to their controls.

Figure 10:
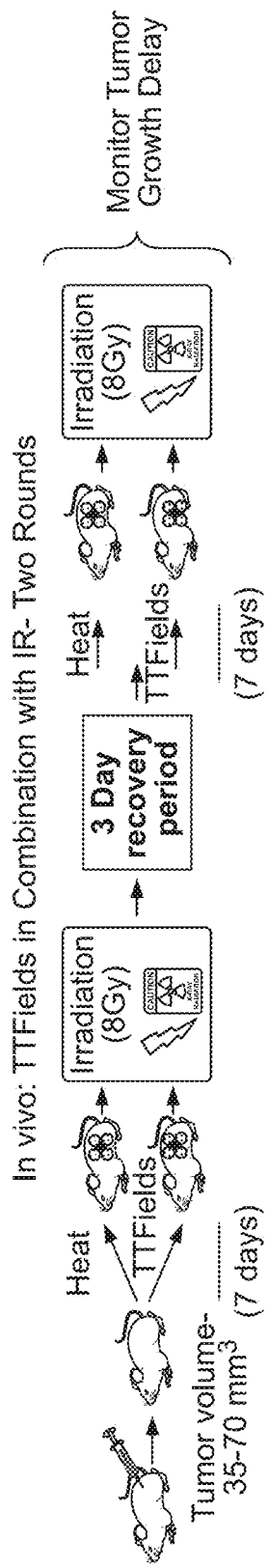
FIG. 10 depicts example effects of a combination of TTFields and irradiation in two rounds, in accordance with exemplary embodiments of the present disclosure.
Figure 10:
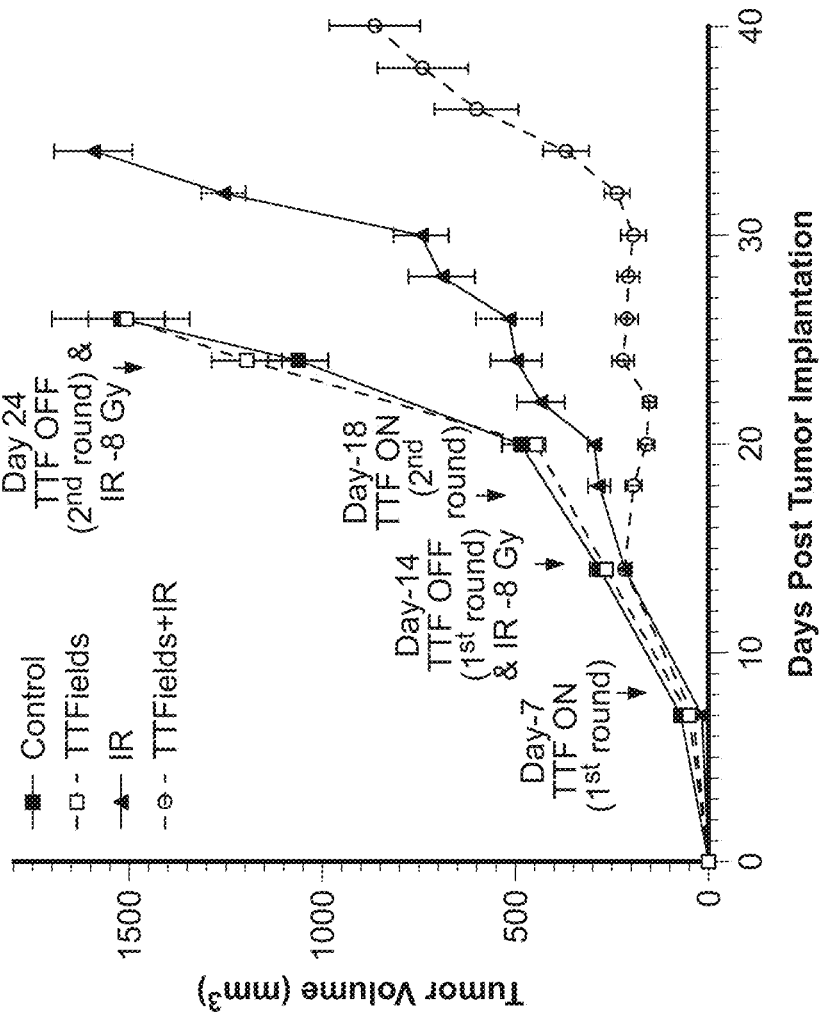

FIG. 10 depicts example effects of a combination of TTFields and irradiation in two rounds, in accordance with exemplary embodiments of the present disclosure. In furtherance of the experiments discussed as it relates to FIG. 9, FIG. 10 depicts an instance where two cycles of TTFields and Radiation treatment combination were applied. TTFields or heat treatments were started when the tumor volumes reached average volume around 40 mm$^3$. After 7 days of treatment (TTFields or Heat) mice were exposed to 8 Gy radiation and mice were allowed to gain body weight in regular cages for 3 days. After 3 days second round of 7 days of treatment (TTFields or Heat) was given to mice and then exposed to 8 Gy radiation. Immediately after second round of Irradiation mice were transferred to regular cages and tumor volumes and body weights were measured every alternative day. One round of TTFields and IR treatment slowed the tumor growth, but the further significant tumor growth inhibition was observed in two rounds of TTFields plus IR treated group mice compared to their controls. Notably, although two rounds of TTFields and IR treatments were administered, several rounds could be delivered to a subject based on one or more factors, including but not limited to, the subject's response to previous rounds of treatment.

It further embodiments, a third round of TTFields would further impact tumor growth delay. Notably, normal tissue response drives clinical use of radiation and every tissue found in a radiation field has a tolerance dose that limited the individual dose as well as the cumulative dose of radiation. As such, one objective would be to minimize the number of radiation doses that the animal (e.g., mice, patient, etc.) would receive as a way to limit the amount of normal tissue irradiated. Therefore, in this instance, given the potential for an enhanced immunogenic response to the combination of radiation and an immune checkpoint inhibitor or TTFields combined with an immune checkpoint inhibitor, the anti-PD-L1 antibody atezolizumab would be added to the radiation/TTFields regimen.

Figure 11:
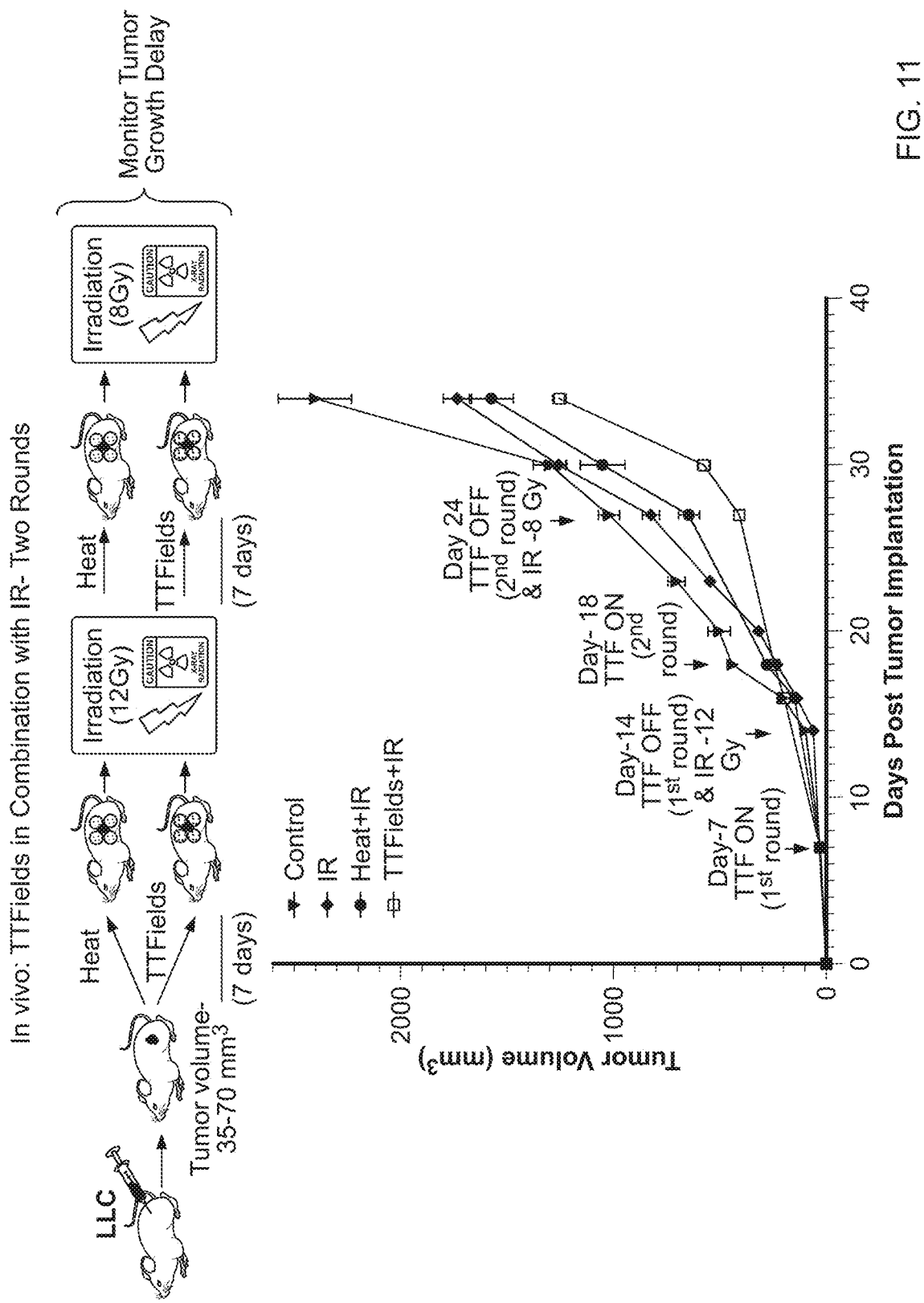
FIG. 11 depicts example effects of a combination of TTFields and irradiation in two rounds, in accordance with exemplary embodiments of the present disclosure.

FIG. 11 depicts example effects of a combination of TTFields and irradiation in two rounds, in accordance with exemplary embodiments of the present disclosure. In furtherance of the experiments discussed as it relates to FIGS. 9-10, FIG. 11 depicts a similar experiment using LLC model exposing the mice for two cycles of TTFields and Radiation treatment combination. TTFields and heat treatments were started when the tumor volumes reached average volume around 40 mm$^3$. After 7 days of treatment (TTFields or Heat) mice were exposed to 12 Gy radiation and mice were allowed to gain body weight in regular cages for 3 days. After 4 days second round of 7 days of treatment (TTFields or Heat) was given to mice and then exposed to 8 Gy radiation. Immediately after second round of Irradiation mice were transferred to regular cages and tumor volumes and body weights were measured every alternative day. It was found that more ulceration and aggressive form of tumor in this model. Accordingly, the results of the experiment suggest that a trend of decreased TGD in TTFields plus IR treated group mice compared to their control it is not as significant as in the MC38 model. Notably, although two rounds of TTFields and IR treatments were administered, several rounds could be delivered to a subject based on one or more factors, including but not limited to, the subject's response to previous rounds of treatment. In addition, various chemotherapy agents could be delivered in between rounds of TTFields and IR treatments. For example, after a second round of TTFields and IR treatments, a subject could be delivered a first chemotherapy agent. Subsequently, the subject could be evaluated to determine the effectiveness of the first treatment of TTFields, IR, and chemotherapy agent. In one instance, if the subject (e.g., the subject's tumor) is found not be responsive (i.e., resistant) to the chemotherapy agent, the subject may be administered a second chemotherapy agent in a third round (or any number of subsequent rounds of treatment) of TTFields and IR treatments. Alternatively, if the first chemotherapy agent is determined to be effective at treating the subject, the subject may be administered the first chemotherapy agent again in a subsequent round of treatment. However, the first chemotherapy agent may be delivered at a different dose or in conjunction with one or more other chemotherapy agents based on the determined effectiveness in an earlier round of treatment.

Figure 12:
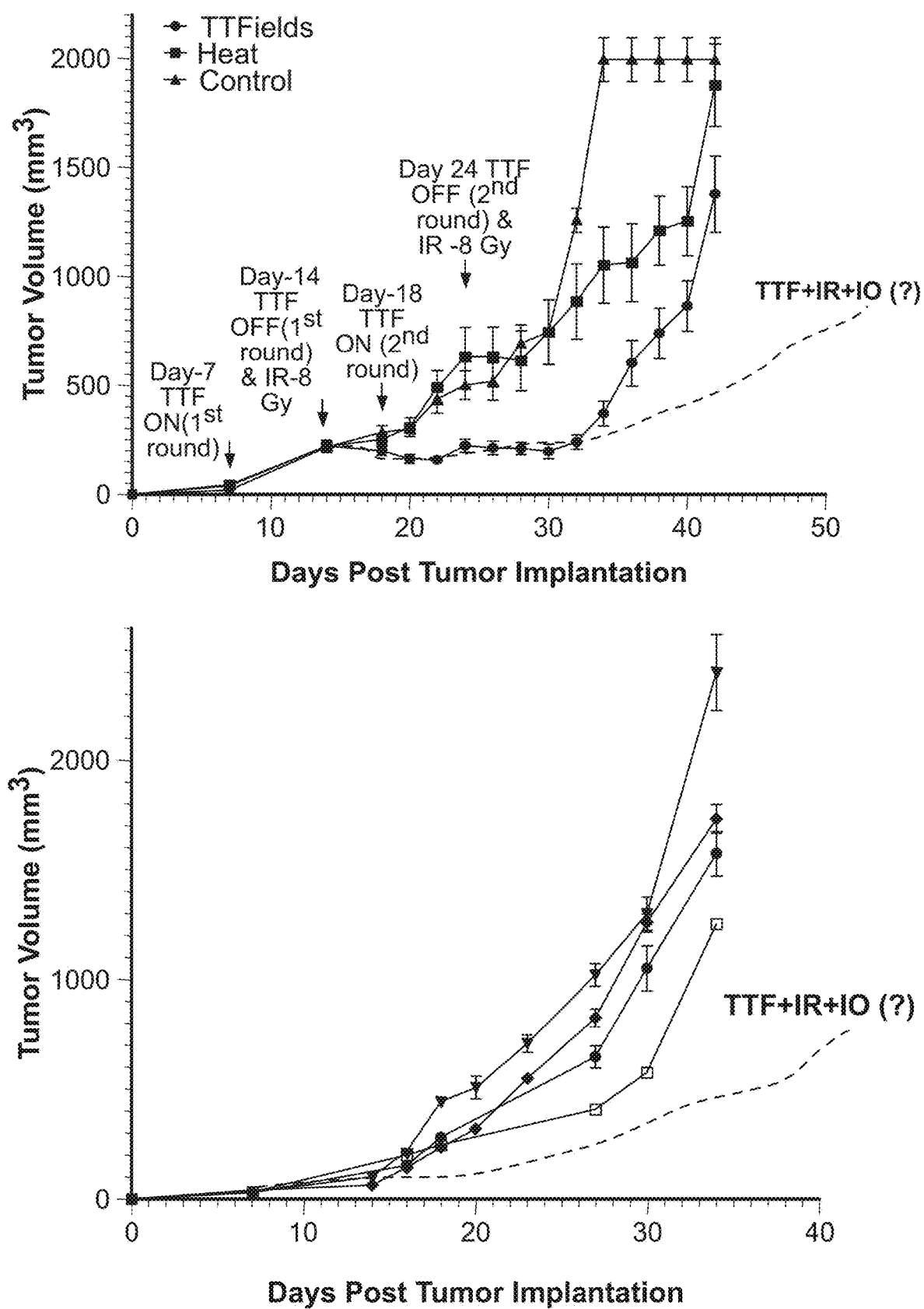
FIG. 12 depicts example effects TTFields and irradiation on tumor volume, in accordance with exemplary embodiments of the present disclosure.

FIG. 12 depicts example effects TTFields and irradiation on tumor volume, in accordance with exemplary embodiments of the present disclosure. For example, FIG. 12 depicts data forecasting the results of a therapeutic combination of TTFields, PULSAR, and one or more additional tumor impairing therapies.

Figure 13:
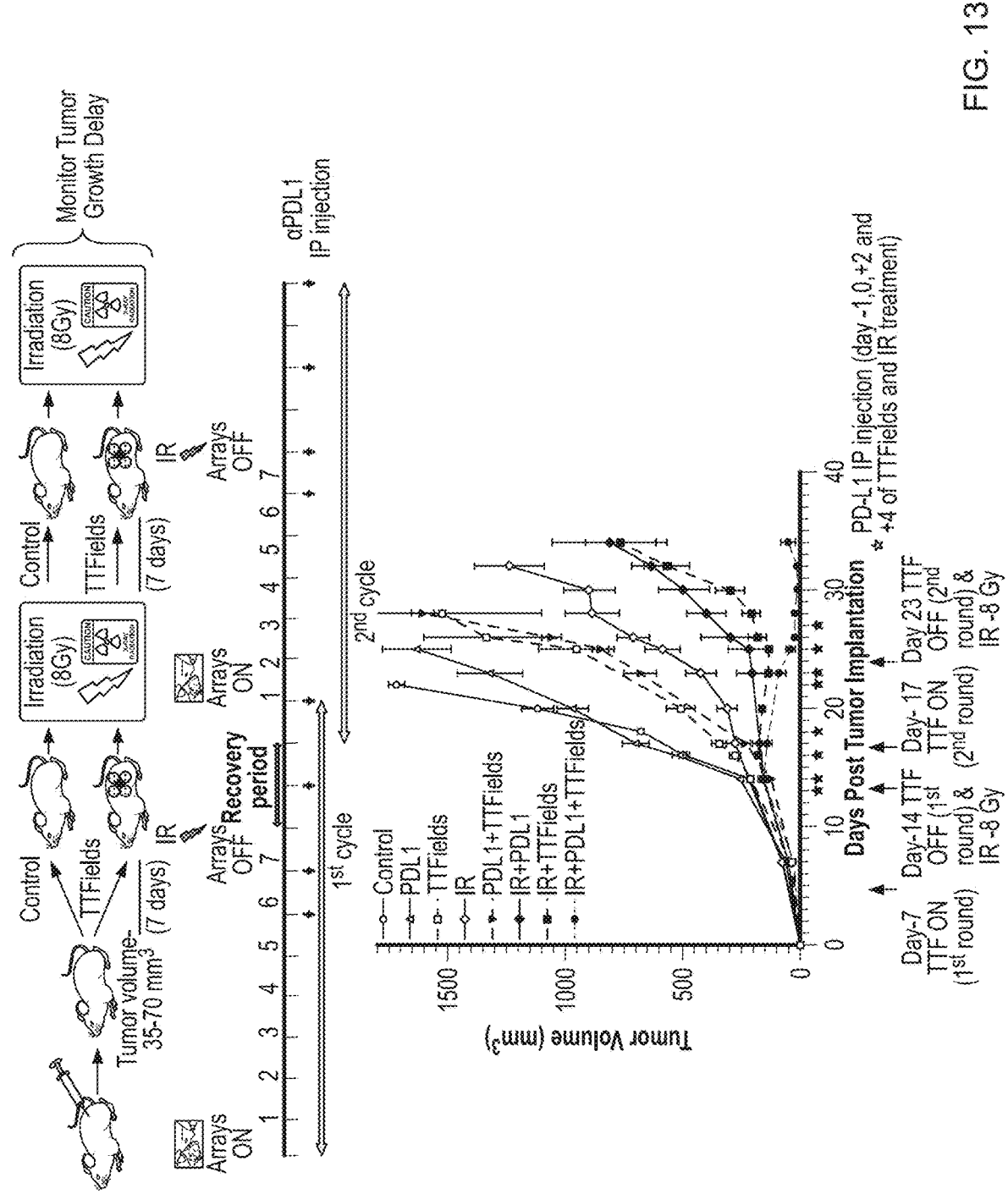
FIG. 13 depicts a tumor growth delay curve, in accordance with exemplary embodiments of the present disclosure.

FIG. 13 a tumor growth delay curve according to one or more example. As depicted, example effects where mice were exposed to 8 Gy of X-rays after 7 days of treatment (TTFields) and allowed to gain body weight for 3 days. Mice were then treated with TTFields for another 7 days, followed by exposure to another 8 Gy of X-rays. At the indicated time points, PD-L1 antibody was subcutaneously injected into specific cohorts of mice while not in the others. There was a substantial tumor growth inhibition observed with TTFields combined with radiation and PD-L1 relative to the groups treated with either TTFields plus PD-L1 antibody or TTFields plus radiation or radiation plus PD-L1 antibody. Furthermore, tumor cure appears to be observed in 3 of 6 mice in the triple combination group of TTFields, radiation, and PD-L1 antibody (as depicted further in FIG. 15). Here, the individual growth delay of each mouse in the triple combination group of TTFields, radiation, and the immune checkpoint inhibitor are described individually. For 3 of the 6 mice, tumors are not readily measurable. This treatment regimen is an exemplary cohort where tumor cure was seen.

Figure 14:
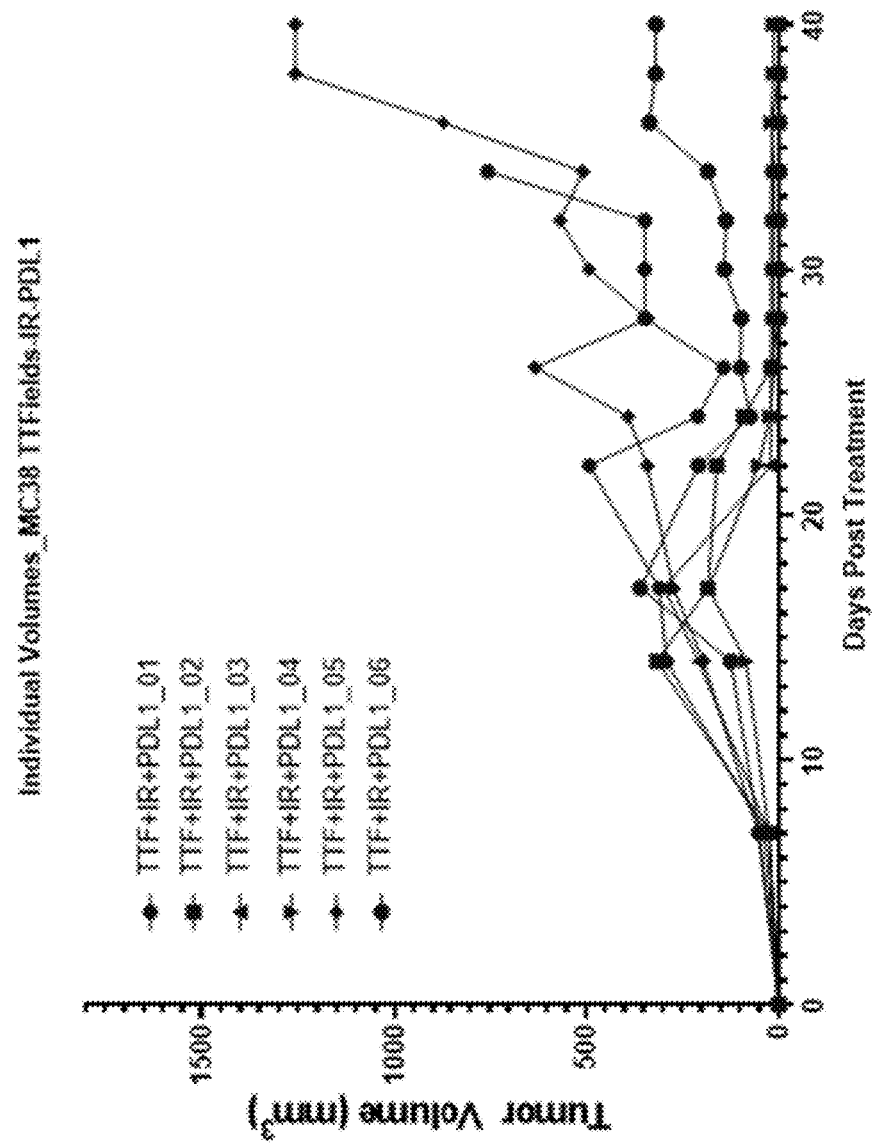
FIG. 14 depicts a tumor growth delay curve, in accordance with exemplary embodiments of the present disclosure.

FIG. 14 depicts a tumor growth delay curve, according to one or more examples. In furtherance of treatment, for example, the treatment discussed in relation to FIG. 13, the tumor size of each patient (e.g., mice) were analyzed over a period of time, post treatment. As depicted, tumor volume for some patients receiving a combination of TTFields, radiation, and PD-L1 antibody, resulted in significant deterioration.

Figure 15:
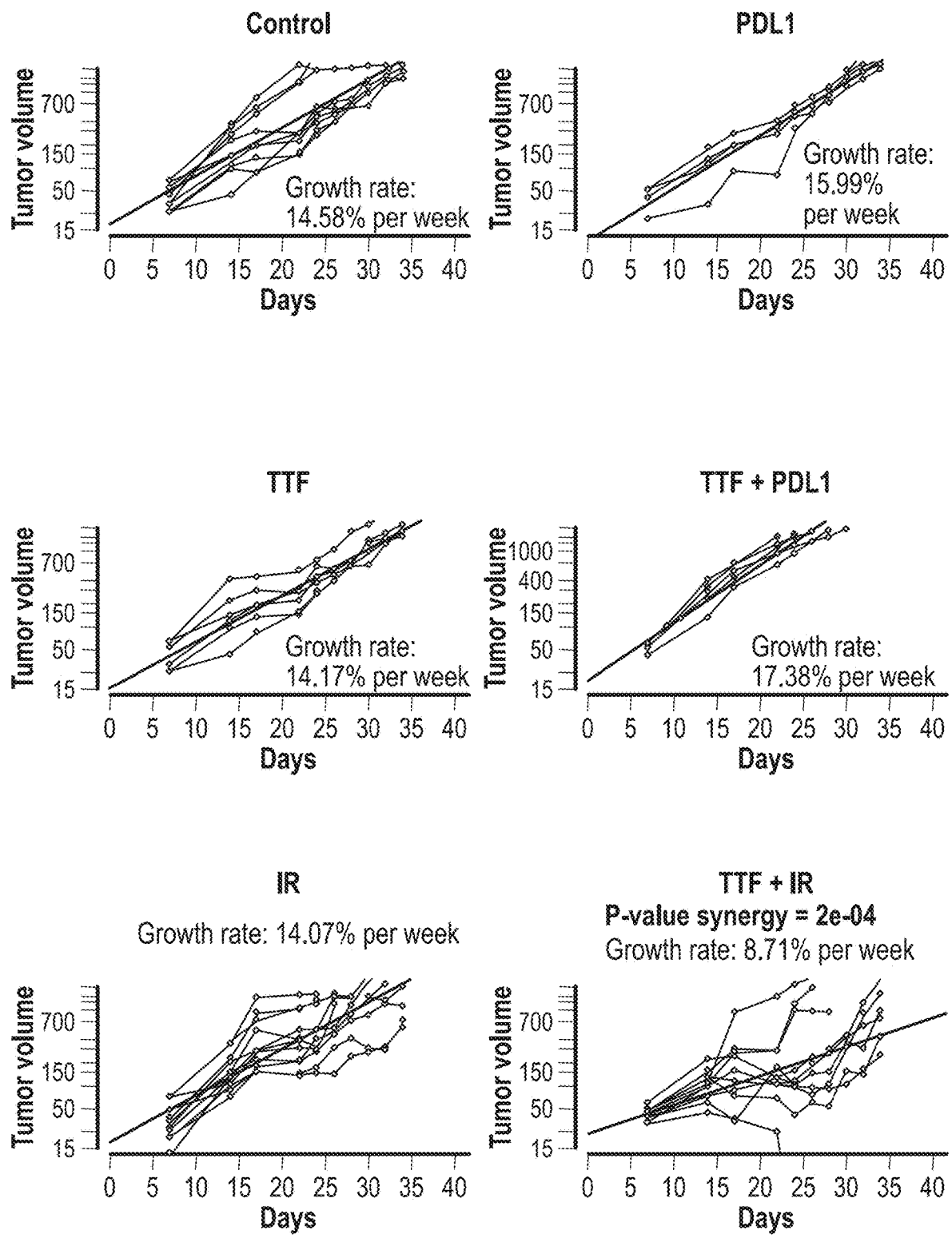
FIG. 15 depicts multiple tumor growth delay curves by individual treatment, in accordance with exemplary embodiments of the present disclosure.
Figure 15:
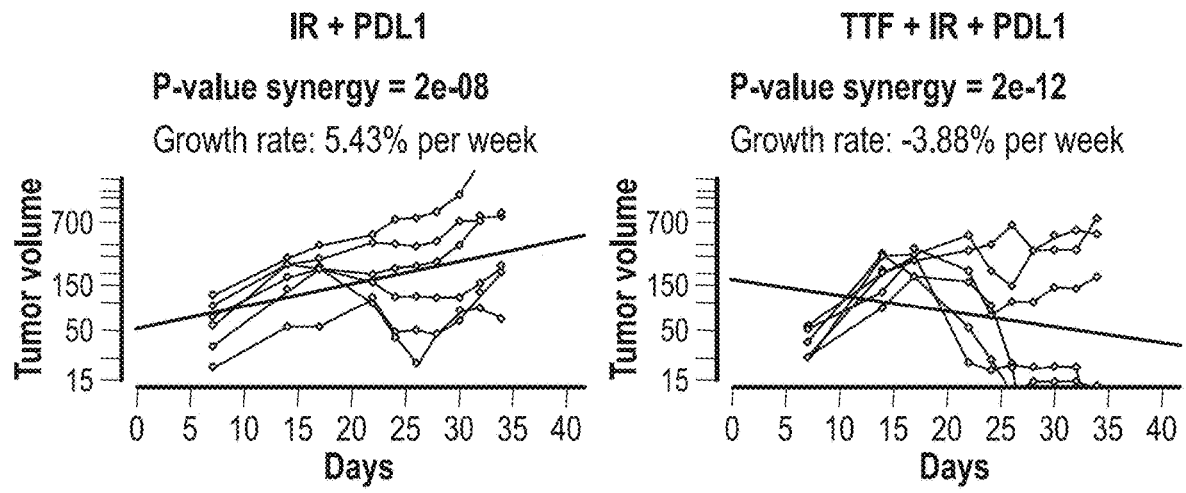

As depicted in FIG. 15, multiple tumor growth delay curves by individual treatment. As depicted, the individual growth delay of a patient (e.g., a mouse) having received the triple combination group of TTFields, radiation, and the immune checkpoint inhibitor, is depicted. Statistical significance: The Bliss test of significance for synergistic effects in combination therapies (as discussed in Demidenko, E., & Miller, T. W. (2019). Statistical Determination of Synergy based on Bliss Definition of Drugs Independence. PloS one, 14 (11), e0224137.https://doi.org/10.1371/journal-.pone.0224137, is hereby incorporated by reference) was used to determine whether there are combinations of TTFields and radiation that are synergistic (i.e., where the effect is greater than the effects would be if the individual independent effects were combined). In this approach, tumor growth delay curves from FIGS. 13 and 14 are replotted in FIG. 15 as log linear functions and a linear regression of the data is applied. Slopes of those regressions are treated as being independent effects and then analyzed to detect synergy for the combination of independent effects. The solid line represents a linear regression whose slope represents tumor growth as a percentage per week. Each independent treatment is plotted as is the control group. Then, combination therapies are plotted. Combination therapies that are synergistic include the combination of two rounds of TTFields and radiation, the combination of radiation with anti-PD-L1, and the triple combination of TTFields, radiation and anti-PD-L1 antibody. The p values that represent statistical significance for these three combinations are depicted in Table 1 of FIG. 15, and they are highly significant. As depicted, TTFields added to radiation results in a combination effect that is synergistic. The addition of TTFields to a model of standard of care, that is, radiation plus the checkpoint inhibitor anti-PD-L1 antibody—the combination of which is also synergistic, results in strong synergy and most importantly tumor cure after only two rounds of radiation including the immune checkpoint inhibitor.

EXEMPLARY APPARATUSES

Figure 16:
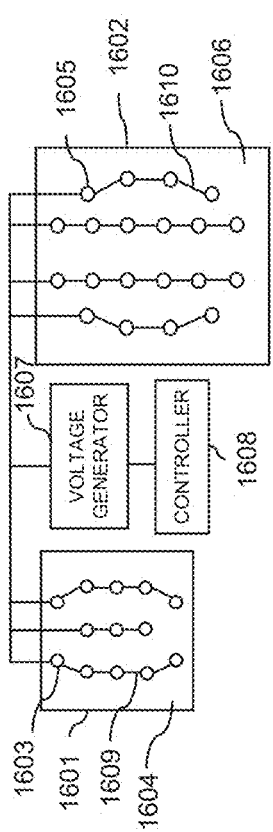
FIG. 16 depicts one example of an apparatus to apply TTFields with modulated electric fields to a subject's body.

FIG. 16 depicts one example of an apparatus to apply TTFields with modulated electric fields to a subject's body. The first transducer 1601 includes 16 electrode elements 1603, which are positioned on the substrate 1604, and the electrode elements 1603 are electrically and mechanically connected to one another through a conductive wiring 1609. The second transducer 1602 includes 20 electrode elements 1605, which are positioned on the substrate 1606, and the electrode elements 1605 are electrically and mechanically connected to one another through a conductive wiring 1610. The first transducer 1601 and the second transducer 1602 are connected to an AC voltage generator 1607 and a controller 1608. The controller 1608 may include one or more processors and memory accessible by the one or more processors. The memory may store instructions that when executed by the one or more processors, control the AC voltage generator 1607 to implement one or more embodiments of the invention. In some embodiments, the AC voltage generator 1607 and the controller 1608 may be integrated in the first transducer 1601 and the second transducer 1602 and form a first electric field generator and a second electric field generator.

Figure 17:
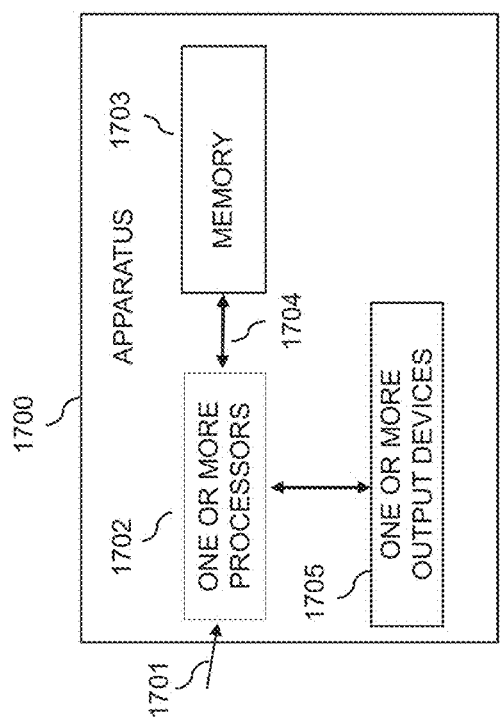
FIG. 17 depicts an example computer apparatus.

FIG. 17 depicts an example computer apparatus for use with the embodiments herein. As an example, the apparatus 1700 may be a computer to implement certain inventive techniques disclosed herein. As an example, the apparatus 1700 may be a controller apparatus to apply TTFields with modulated electric fields for the embodiments herein. The apparatus 1700 may be used as the controller 1608 of FIG. 13. The apparatus 1700 may include one or more processors 1702, one or more output devices 1705, and a memory 1703.

In one example, based on input 1701, the one or more processors generate control signals to control the voltage generator to implement an embodiment of the invention. In one example, the input 1701 is user input. In another example, the input 1701 may be from another computer in communication with the apparatus 1700. The output devices 1705 may provide the status of the operation of the invention, such as transducer selection, voltages being generated, and other operational information. The output devices 1705 may provide visualization data according to certain embodiments of the invention.

The memory 1703 is accessible by the one or more processors 1702 via the link 1704 so that the one or more processors 1702 can read information from and write information to the memory 1703. The memory 1703 may store instructions that when executed by the one or more processors 1702 implement one or more embodiments of the invention.

Numerous modifications, alterations, and changes to the described embodiments are possible without departing from the scope of the present invention defined in the claims. It is intended that the present invention not be limited to the described embodiments but that it has the full scope defined by the language of the following claims and equivalents thereof.

What is claimed is:

1. A method of treating a tumor in a subject, comprising:
    applying a tumor treating field to the tumor at a frequency between 50 kHz and approximately 1,000 kHz; and
    delivering personalized ultra-fractionated adaptive radiotherapy to the subject comprising:
        administering a first pulse dose of radiation to the tumor within the subject,
        administering a second pulse dose of radiation to the tumor, wherein the second pulse dose is administered after an observation period, the observation period having a duration of at least 7 days, and
        concurrently treating the subject with an immunotherapy.

2. The method of claim 1, wherein the tumor treating field establishes a conditional vulnerability with the tumor.

3. The method of claim 1, wherein the first and second pulse doses of radiation are ablative.

4. The method of claim 3 further comprising, in response to administering the first pulse dose, determining at least one of a level of radiation for the second pulse dose, the duration of the observation period, and a target field for the second pulse dose.

5. The method of claim 4, wherein the first pulse dose of radiation is 8 Gy.

6. The method of claim 4 further comprising, analyzing radiomic features and biologic features.

7. The method of claim 6, wherein the biologic features comprise at least one of target tissue vascularity, normal tissue vascularity, target tissue oxygenation status, normal tissue oxygenation status, target tissue cytokine profile, normal tissue cytokine profile, target tissue gene expression, normal tissue gene expression, circulating tumor DNA indicative of tumor response to therapy, the levels of circulating tumor cells, target tissue receptor expression, normal tissue receptor expression, target tissue white blood cell infiltration, normal tissue white blood cell infiltration, tumor markers, tumor burden, systemic immune status, changes in subject health, and changes in patient weight.

8. The method of claim 6, wherein the radiomic features comprise at least one anatomical imaging characteristics, functional imaging characteristics, and metabolic imaging characteristics.

9. The method of claim 1, wherein an intensity of the tumor treating field is between approximately 1 V/cm and approximately 4 V/cm.

10. The method of claim 1, wherein the frequency of an alternating electric field is between 80 and 300 kHz.

11. The method of claim 1, wherein the tumor treating field is applied for 7 continuous days.

12. The method of claim 4, wherein the second pulse dose is between 15 Gy and 50 Gy.

13. The method of claim 1, further comprising delivering a DNA replication stress inducing agent to the tumor.

14. The method of claim 13, wherein the DNA replication stress inducing agent comprises at least one of a platinum compound, an alkylating agent, a wee1 inhibitor, a Chk1 inhibitor, a thymidylate synthase inhibitor, a ribonucleotide reductase inhibitor, Topoisomerase I inhibitor, Topoisomerase II inhibitor, a maternal embryonic leucine zipper kinase (MELK) inhibitor, or a NEDD8-activating enzyme (NAE) inhibitor.

15. The method of claim 14, wherein the DNA replication stress inducing agent is delivered to the tumor comprising a platinum compound, the platinum compound further comprising at least one of cisplatin, carboplatin, oxaliplatin, dicycoplatin, or lipoplatin,
    wherein if the DNA replication stress inducing agent delivered to the tumor is the alkylating agent, the alkylating agent comprises at least one of cyclophosphamide or temozolomide,
    wherein if the DNA replication stress inducing agent delivered to the tumor is the wee1 inhibitor, the wee1 inhibitor comprises at least one of Adavosertib-MK1775 or PD0166285,
    wherein if the DNA replication stress inducing agent delivered to the tumor is the Chk1 inhibitor, the Chk1 inhibitor comprises at least one of UCN-01, LY2606368, SAR-020106, AZD7762, or PD0166285,
    wherein if the DNA replication stress inducing agent delivered to the tumor is the thymidylate synthase inhibitor, the thymidylate synthase inhibitor comprises at least one of 5-FU or pemetrexed,
    wherein if the DNA replication stress inducing agent delivered to the tumor is the ribonucleotide reductase inhibitor, the ribonucleotide reductase inhibitor comprises gemcitabine,
    wherein if the DNA replication stress inducing agent delivered to the tumor is the Topoisomerase I inhibitor, the Topoisomerase I inhibitor comprises at least one of Irinotecan or Topotecan,
    wherein if the DNA replication stress inducing agent delivered to the tumor is the Topoisomerase II inhibitor, the Topoisomerase II inhibitor comprises at least one of etoposide or doxorubicin,
    wherein if the DNA replication stress inducing agent delivered to the tumor is the MELK inhibitor, the MELK inhibitor comprises OTS167, and
    wherein if the DNA replication stress inducing agent delivered to the tumor is the NAE inhibitor, the NAE inhibitor comprises MLN4924.

16. The method of claim 13, further comprising delivering an additional DNA replication stress inducing agent to the tumor.

17. The method of claim 1, further comprising delivering at least one of an E2F inhibitor, a CDK4/6 inhibitor, or a PARP inhibitor.

18. The method of claim 17, wherein the E2F inhibitor is delivered to the tumor, and wherein the E2F inhibitor is HLM006474.

19. A method of treating a tumor in a subject, comprising:
    applying a tumor treating field to the tumor at a frequency between 50 kHz and approximately 1,000 kHz;
    delivering personalized ultra-fractionated adaptive radiotherapy to the subject; and delivering a DNA replication stress inducing agent to the tumor.

\* \* \* \* \*